(12) United States Patent
Gonzales et al.

(10) Patent No.: US 9,163,201 B2
(45) Date of Patent: Oct. 20, 2015

(54) LIQUID DETERGENT COMPOSITION WITH ABRASIVE PARTICLES

(71) Applicant: The Procter & Gamble Company, Cincinnati, OH (US)

(72) Inventors: Denis Alfred Gonzales, Brussels (BE); Michael Leslie Groombridge, Newcastle (GB); Michael McDonnell, Northumberland (GB); Aicha Dkidak, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 75 days.

(21) Appl. No.: 14/051,535

(22) Filed: Oct. 11, 2013

(65) Prior Publication Data

US 2014/0105831 A1   Apr. 17, 2014

(30) Foreign Application Priority Data

Oct. 15, 2012   (EP) ..................................... 12188500

(51) Int. Cl.

| | | |
|---|---|---|
| C11D 17/00 | (2006.01) | |
| A61Q 11/00 | (2006.01) | |
| A61K 8/19 | (2006.01) | |
| A61K 8/02 | (2006.01) | |
| C11D 3/14 | (2006.01) | |
| A61Q 19/10 | (2006.01) | |

(52) U.S. Cl.
CPC ... *C11D 3/14* (2013.01); *A61K 8/19* (2013.01); *A61Q 11/00* (2013.01); *A61Q 19/10* (2013.01); *C11D 17/0013* (2013.01)

(58) Field of Classification Search
CPC ... A61K 2800/28; A61K 8/0279; A61K 8/19; A61Q 11/00; C11D 3/14; C11D 17/0013
USPC .................................. 424/401; 510/397, 395
See application file for complete search history.

(56) References Cited

U.S. PATENT DOCUMENTS

| | | |
|---|---|---|
| 1,621,906 A | 3/1927 | Schless |
| 2,082,275 A | 6/1937 | Daimler et al. |
| 2,084,632 A | 6/1937 | Ellis |
| 2,255,082 A | 9/1941 | Orthner et al. |
| 2,438,091 A | 3/1948 | Lynch |
| 2,528,378 A | 10/1950 | Mannheimer |
| 2,658,072 A | 11/1953 | Kosmin |
| 2,702,279 A | 2/1955 | Funderburk et al. |
| 3,070,510 A | 12/1962 | Cooley et al. |
| 3,586,715 A | 6/1971 | Smeets |
| 3,767,791 A * | 10/1973 | Cordon .......................... 424/49 |
| 3,812,044 A | 5/1974 | Connor et al. |
| 3,915,903 A | 10/1975 | Wise |
| 3,929,678 A | 12/1975 | Laughlin et al. |
| 3,985,668 A | 10/1976 | Hartman |
| 4,025,444 A | 5/1977 | Murphy et al. |
| 4,051,056 A | 9/1977 | Hartman |
| 4,088,620 A | 5/1978 | Nihongi et al. |
| 4,102,992 A | 7/1978 | Davis |
| 4,235,732 A * | 11/1980 | Beyer ............................. 510/369 |
| 4,240,919 A | 12/1980 | Chapman |
| 4,298,490 A | 11/1981 | Lange et al. |
| 4,309,316 A | 1/1982 | Lange et al. |
| 4,473,611 A | 9/1984 | Haq |
| 4,481,126 A | 11/1984 | Trinh et al. |
| 4,537,604 A | 8/1985 | Dawson |
| 4,565,644 A | 1/1986 | Smith et al. |
| 4,565,647 A | 1/1986 | Llenado |
| 4,581,385 A | 4/1986 | Smith et al. |
| 4,657,692 A | 4/1987 | Choy et al. |
| 4,663,069 A | 5/1987 | Llenado |
| 4,676,920 A | 6/1987 | Culshaw |
| 4,704,233 A | 11/1987 | Hartman et al. |
| 4,767,563 A | 8/1988 | De Buzzaccarini |
| 4,772,425 A | 9/1988 | Chirash et al. |
| 4,842,763 A | 6/1989 | Troger et al. |
| 4,906,396 A | 3/1990 | Falholt et al. |
| 5,287,207 A | 2/1994 | Mulkens et al. |
| 5,500,451 A | 3/1996 | Goldman et al. |
| 5,776,872 A | 7/1998 | Giret et al. |
| 5,776,878 A | 7/1998 | Theon |
| 5,798,505 A | 8/1998 | Lee |
| 5,821,214 A | 10/1998 | Weibel |
| 5,830,445 A | 11/1998 | Bouillon et al. |
| 5,883,062 A | 3/1999 | Addison et al. |
| 5,898,026 A | 4/1999 | Yianakopoulos et al. |
| 5,906,973 A | 5/1999 | Ouzounis et al. |

(Continued)

FOREIGN PATENT DOCUMENTS

| | | |
|---|---|---|
| DE | 24 10 425 A1 | 10/1974 |
| DE | 10 2004 038771 A1 | 8/2005 |

(Continued)

OTHER PUBLICATIONS

U.S. Appl. No. 13/517,837, filed Jun. 14, 2012, Gonzales, et al.
U.S. Appl. No. 13/517,728, filed Jun. 14, 2012, Gonzales, et al.
U.S. Appl. No. 13/526,592, filed Jun. 19, 2012, Gonzales, et al.
U.S. Appl. No. 13/526,596, filed Jun. 19, 2012, Gonzales, et al.
U.S. Appl. No. 13/517,746, filed Jun. 14, 2012, Gonzales, et al.
U.S. Appl. No. 13/526,605, filed Jun. 19, 2012, Gonzales, et al.
U.S. Appl. No. 13/526,613, filed Jun. 19, 2012, Gonzales, et al.
U.S. Appl. No. 13/517,762, filed Jun. 14, 2012, Perez-Prat Vinuesa, et al.
U.S. Appl. No. 13/621,858, filed Sep. 18, 2012, Gonzales, et al.

(Continued)

*Primary Examiner* — Frederick Krass
*Assistant Examiner* — Tracy Liu
(74) *Attorney, Agent, or Firm* — Abbey A. Lopez

(57) ABSTRACT

A composition comprising abrasive particles derived from inorganic-based foam, wherein said abrasive particles are non-spherical having a form factor from 0.1 to 0.6 and a solidity from 0.3 to 0.9, and wherein said abrasive particles comprise one or more inorganic materials and have a MOHs hardness of from 1 to 4.

13 Claims, 2 Drawing Sheets

(56) References Cited

U.S. PATENT DOCUMENTS

| | | |
|---|---|---|
| 6,008,181 A | 12/1999 | Cripe et al. |
| 6,020,303 A | 2/2000 | Cripe et al. |
| 6,060,443 A | 5/2000 | Cripe et al. |
| 6,080,707 A | 6/2000 | Glenn et al. |
| 6,132,212 A | 10/2000 | Horiguchi et al. |
| 6,221,829 B1 | 4/2001 | Symes et al. |
| 6,242,405 B1 | 6/2001 | Lykke et al. |
| 6,265,363 B1 | 7/2001 | Viscovitz |
| 6,268,325 B1 | 7/2001 | Luciani et al. |
| 6,274,540 B1 | 8/2001 | Scheibel et al. |
| 6,299,746 B1 | 10/2001 | Conte et al. |
| 6,306,817 B1 | 10/2001 | Kott et al. |
| 6,359,031 B1 | 3/2002 | Lykke et al. |
| 6,369,121 B1 | 4/2002 | Catalfamo et al. |
| 6,444,716 B1 | 9/2002 | Hird et al. |
| 6,514,926 B1 | 2/2003 | Kott et al. |
| 6,525,233 B1 | 2/2003 | Connor et al. |
| 6,537,957 B1 | 3/2003 | Cardola et al. |
| 6,566,319 B1 | 5/2003 | Scheibel et al. |
| 6,583,096 B1 | 6/2003 | Kott et al. |
| 6,593,285 B1 | 7/2003 | Scheibel et al. |
| 6,602,840 B1 | 8/2003 | Scheibel et al. |
| 6,699,963 B2 | 3/2004 | Noda et al. |
| 6,749,066 B2 | 6/2004 | Bergman |
| 6,759,377 B2 | 7/2004 | Hackenthal et al. |
| 6,767,878 B1 | 7/2004 | Paye et al. |
| 6,808,759 B1 | 10/2004 | Okumura et al. |
| 6,858,216 B2 | 2/2005 | Schulze zur Wiesche et al. |
| 2,384,243 A1 | 12/2007 | Cook et al. |
| 7,393,820 B2 | 7/2008 | Soldanski et al. |
| 7,713,921 B2 | 5/2010 | Boutique et al. |
| 7,994,111 B2 | 8/2011 | Caggioni et al. |
| 2002/0137647 A1 | 9/2002 | Hackenthal et al. |
| 2002/0166832 A1 | 11/2002 | Silud et al. |
| 2002/0173243 A1 | 11/2002 | Costas et al. |
| 2003/0176934 A1 | 9/2003 | Noda et al. |
| 2003/0215417 A1 | 11/2003 | Uchiyama et al. |
| 2004/0216388 A1 | 11/2004 | Mathur et al. |
| 2004/0266645 A1 | 12/2004 | Albrecht et al. |
| 2005/0065056 A1 | 3/2005 | Cook et al. |
| 2005/0130873 A1 | 6/2005 | Cheung et al. |
| 2005/0170979 A1 | 8/2005 | Massaro et al. |
| 2005/0201965 A1 | 9/2005 | Kuhlman et al. |
| 2006/0011885 A1 | 1/2006 | Christmas et al. |
| 2006/0094635 A1 | 5/2006 | Pereira |
| 2006/0177488 A1 | 8/2006 | Caruso et al. |
| 2007/0006391 A1 | 1/2007 | Ghosh et al. |
| 2007/0010415 A1 | 1/2007 | Kinscherf et al. |
| 2007/0041927 A1 | 2/2007 | Blaeser et al. |
| 2007/0043147 A1 | 2/2007 | Higgins et al. |
| 2007/0135645 A1 | 6/2007 | Ignatyev et al. |
| 2007/0138671 A1 | 6/2007 | Anastasiou et al. |
| 2007/0157948 A1* | 7/2007 | Gonzales et al. .................. 134/6 |
| 2007/0167345 A1 | 7/2007 | Soldanski et al. |
| 2007/0191256 A1 | 8/2007 | Fossum et al. |
| 2007/0270730 A1 | 11/2007 | Rische et al. |
| 2008/0013972 A1 | 1/2008 | De Almeida et al. |
| 2008/0108714 A1 | 5/2008 | Swazey et al. |
| 2008/0149137 A1 | 6/2008 | Steinbrenner et al. |
| 2008/0248144 A1 | 10/2008 | Guenter et al. |
| 2009/0096121 A1* | 4/2009 | Azzi .............................. 264/44 |
| 2009/0176935 A1 | 7/2009 | Boeckh et al. |
| 2009/0253816 A1 | 10/2009 | Nascimento et al. |
| 2009/0291306 A1 | 11/2009 | Quadbeck-Seeger |
| 2009/0325837 A1 | 12/2009 | Mundschau et al. |
| 2010/0081604 A1 | 4/2010 | Barger et al. |
| 2010/0081605 A1 | 4/2010 | Barger et al. |
| 2010/0081606 A1 | 4/2010 | Barger et al. |
| 2010/0127203 A1* | 5/2010 | Ulanova et al. ................ 252/62 |
| 2010/0197553 A1 | 8/2010 | Barnabas et al. |
| 2011/0021398 A1 | 1/2011 | Allef et al. |
| 2011/0039744 A1 | 2/2011 | Heath et al. |
| 2011/0150787 A1 | 6/2011 | Gonzales et al. |
| 2011/0150788 A1 | 6/2011 | Gonzales et al. |
| 2011/0150949 A1 | 6/2011 | Gonzales et al. |
| 2011/0150950 A1 | 6/2011 | Gonzales et al. |
| 2011/0150951 A1 | 6/2011 | Gonzales et al. |
| 2011/0178196 A1 | 7/2011 | Steinke et al. |
| 2011/0189414 A1 | 8/2011 | Whitehouse |
| 2011/0262371 A1 | 10/2011 | Deleersnyder et al. |
| 2011/0262504 A1 | 10/2011 | Deleersnyder et al. |
| 2011/0287105 A1 | 11/2011 | Gittleman |
| 2012/0029519 A1 | 2/2012 | Sengun et al. |
| 2012/0066851 A1 | 3/2012 | Gonzales et al. |
| 2012/0071378 A1 | 3/2012 | Gonzales et al. |
| 2012/0071379 A1 | 3/2012 | Gonzales et al. |
| 2012/0071380 A1 | 3/2012 | Gonzales et al. |
| 2012/0071383 A1 | 3/2012 | Perez-Prat Vinuesa et al. |
| 2012/0121669 A1* | 5/2012 | Fontana et al. ............... 424/401 |
| 2012/0202730 A1 | 8/2012 | Allef et al. |
| 2013/0072417 A1 | 3/2013 | Perez-Prat Vinuesa et al. |

FOREIGN PATENT DOCUMENTS

| | | |
|---|---|---|
| DE | 10 2005 023801 A1 | 11/2006 |
| EP | 1 136 063 A2 | 9/2001 |
| EP | 1 460 125 A1 | 9/2004 |
| GB | 2 001 099 A | 1/1979 |
| GB | 2 126 999 A | 4/1984 |
| GB | 2 145 729 A | 4/1985 |
| JP | 59192526 A | 10/1984 |
| JP | 10025239 A | 1/1998 |
| JP | 2005 296822 A | 10/2005 |
| JP | 2007 077311 A | 3/2007 |
| JP | 2009 160717 A | 7/2009 |
| WO | WO 91/14420 A1 | 10/1991 |
| WO | WO 99/05084 A1 | 2/1999 |
| WO | WO 99/52500 A1 | 10/1999 |
| WO | WO 01/31110 A1 | 5/2001 |
| WO | WO 02/38720 A1 | 5/2002 |
| WO | WO 2004/071483 A1 | 8/2004 |
| WO | WO 2008/109270 A1 | 9/2008 |

OTHER PUBLICATIONS

ASTM Designation: F1877-05 Jun. 10, 2009; Standard Practice for Characterization of Particles; 14 pages; chapter 11.3.6; Section 11.3.2.

International Standard; ISO 9276-6:2008(E) section 8.2; section 7; Representation of results of particle size analysis—Part 6: Descriptive and quantitative representation of particle shape and morphology.

"Vegetable Ivory", W.P. Armstrong, (http://waynesword.palomar.edu/pljan99.htm).

"Phytelephas", Wikipedia.org (http://en.wikipedia.org/wiki/Phytelephas).

* cited by examiner

LIQUID DETERGENT COMPOSITION WITH ABRASIVE PARTICLES

FIELD OF THE INVENTION

The present invention relates to liquid or paste-like compositions comprising abrasive particles comprising one or more inorganic materials. Liquid compositions are typically detergent or non-detergent, preferably detergent, compositions for treating, typically cleaning and/or cleansing, a surface. The surfaces are typically selected from the group consisting of inanimate and animate surfaces, including hard surfaces that can be found in and around the house or industry and/or commercial, institutional and industrial environments, dish surfaces, teeth hard and/or soft tissue surfaces of the oral cavity, such as teeth, gums, tongue and buccal surfaces, human and animal skin, car and vehicles surfaces and the like.

BACKGROUND OF THE INVENTION

Scouring compositions such as particulate compositions or liquid (incl. gel, paste-type) compositions containing abrasive components are well known in the art. Such compositions are used for cleaning and/or cleansing a variety of surfaces; especially those surfaces that tend to become soiled with difficult to remove stains and soils.

Amongst the currently known scouring compositions, the most popular ones are based on abrasive particles either from natural, or organic origin although with shapes varying from spherical to irregular and come in the form of liquid composition having a creamy consistency with the abrasive particles suspended therein.

A need however exists in improving the weight efficiency of known scouring compositions to further improve the cleaning of a surface, whilst providing good surface safety, and further enabling easier suspension of the particles in the liquid matrix.

It is thus an objective of the present invention to provide a liquid cleaning and/or cleansing composition suitable to clean/cleanse a variety of surfaces, including inanimate and animate surfaces, such hard surfaces in and around the house, dish surfaces, hard and soft tissue surface of the oral cavity, such as teeth, gums, tongue and buccal surfaces, human and animal skin, etc., wherein the composition provides good cleaning/cleansing performance, whilst providing a good surface safety profile and particle suspension.

It has been found that the above objective can be met by the composition according to the present invention.

It is an advantage of the compositions according to the present invention that they may be used to clean/cleanse inanimate and animate surfaces made of a variety of materials like glazed and non-glazed ceramic tiles, enamel, stainless steel, Inox®, Formica®, vinyl, no-wax vinyl, linoleum, melamine, glass, plastics, painted surfaces, human and animal skin, hair, hard and soft tissue surface of the oral cavity, such as teeth enamel, gums, tongue and buccal surfaces, and the like.

A further advantage of the present invention is that in the compositions herein, the particles can be formulated at very low levels, whilst still providing the above benefits. Indeed, in general for other technologies, generally high levels by weight of abrasive particles are needed to reach good cleaning/cleansing performance, thus leading to high formulation and process cost, difficult rinse and end cleaning profiles, as well as limitation for aesthetics and a pleasant hand feel of the cleaning/cleansing composition.

SUMMARY OF THE INVENTION

A composition comprising abrasive particles derived from inorganic-based foam, wherein said abrasive particles are non-spherical having a form factor of less than 0.6 and a solidity of less than 0.9, and wherein said abrasive particles comprise one or more inorganic materials and have a MOHs hardness of from 1 to 4.

In another aspect, the present invention relates to a process thereof.

In yet another aspect, the present invention relates to the use of abrasive particles, preferably comprising a hollow core having a perfume and/or malodor counteractant therein, in a liquid composition, to mask or elimintate malodor from a surface.

DETAILED DESCRIPTION OF THE INVENTION

Figure 1:
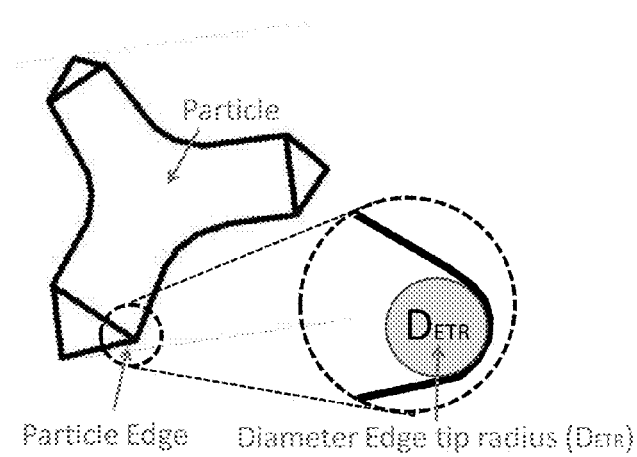
FIG. 1 is an illustration of tip radius.

As used herein "grease" means materials comprising at least in part (i.e., at least 0.5 wt % by weight of the grease) saturated and unsaturated fats and oils, preferably oils and fats derived from animal sources, such as beef and/or chicken; and/or vegetable sources.

As used herein "shelf stable" means a neat hand dishwashing liquid detergent composition that under ambient conditions does not phase separate for at least two weeks, preferably for at least six months, and more preferably never.

As used herein "household hard surface or hard surface", it is meant herein any kind of surface typically found in and around houses like kitchens, bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, Inox®, Formica®, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments. Such surfaces also include dish or dishware surfaces.

As used herein "dish or dishware surfaces" it is meant herein any kind of surfaces found in dish cleaning, such as dishes, cutlery, cutting boards, pans, and the like. Such dish surfaces may be found both in private households as well as in commercial, institutional and industrial environments.

As used herein "hand skin care benefit" means any benefit relating to hand skin appearance (such as smoothness, elasticity, absence of redness and absence of lines and wrinkles), skin feel (such as softness and suppleness), and skin moisture level.

As used herein "exfoliation or mild skin exfoliation" means removal of dead skin cells from the outermost layer of the skin whilst minimizing the risk of over-exfoliating the skin, which may otherwise result in damaged and red hands.

As used herein "suds profile" means amount of sudsing (high or low) and the persistence of sudsing (sustained or prevention) throughout the washing process resulting from the use of the liquid detergent composition of the present composition. Liquid dishwashing detergent compositions require high sudsing and sustained suds. This is particularly important with respect to liquid dishwashing detergent compositions as the consumer uses high sudsing as an indicator of the performance of the detergent composition and as an indicator that the wash solution still contains active detergent ingredients. The consumer usually renews the wash solution when the sudsing subsides. Thus, a low sudsing dishwashing liquid detergent composition will tend to be replaced by the consumer more frequently than is necessary because of the low sudsing level. As used herein "surface safety" means that the surface to be cleaned is not damaged by the composition of the present invention as seen by the lack of visual scratching on the dishware surface after cleaning.

As used herein "stubborn soil" means strongly adhering soils that are typically very difficult to remove. Such soils comprise but are not limited to burnt-on and/or baked-on food residues.

As used herein "inorganic-comprising particles or inorganic foam particles" means particles formed by shearing, grinding, milling, and/or graining, preferably grinding, inorganic-based foam.

As used herein "inorganic" means any inorganic material having a specific gravity of from 1 to 3, preferably from 1 to 2.5, more preferably from 1 to 2 and a Mohs hardness ranging from 1 to 4, preferably from 1.5 to 3.5, preferably from 2 to 3 and more preferably from 2.5 to 3.

As used herein "inorganic-based foam or inorganic foam" means a foam structure generated with a material essentially consisting of, preferably consisting of, one or more inorganic materials. Such structure having a lightweight foam form resulting from suitable foaming and manufacturing process known in the art such as but non exhaustive introduction of gas bubble, emulsification, replicate or template foaming optionally followed by curing and/or drying.

Various embodiments will now be described to provide an overall understanding of the principles of the structure, function, manufacture, and use of the particles, compositions and methods disclosed herein. One or more examples of these embodiments are illustrated in the accompanying drawings. Those of ordinary skill in the art will understand that features described or illustrated in connection with one example embodiment can be combined with the features of other example embodiments without generalization from the present disclosure.

The Composition

The compositions, preferably a liquid or paste detergent composition, according to the present invention are designed as cleaners/cleansers for a variety of inanimate and animate surfaces and comprise one or more active ingredients and abrasive particles. Preferably, the compositions herein are suitable for cleaning/cleansing surfaces selected from the group consisting of inanimate surfaces and animate surfaces.

In a preferred embodiment, the compositions herein are suitable for cleaning/cleansing inanimate surfaces selected from the group consisting of household hard surfaces; dish surfaces; surfaces like leather or synthetic leather; and automotive vehicle surfaces.

In an another preferred embodiment, the compositions herein are suitable for cleaning/cleansing animate surfaces selected from the group consisting of human skin; animal skin; human hair; animal hair; and teeth.

The compositions according to the present invention are liquid or paste compositions as opposed to a solid or a gas. Liquid compositions include compositions having a water-like viscosity as well as thickened compositions, such as gels.

In a preferred embodiment herein, the liquid compositions herein are aqueous compositions. Therefore, they may comprise from 65% to 99.5% by weight of the total composition of water, preferably from 75% to 98% and more preferably from 80% to 95%.

In another preferred embodiment herein, the liquid compositions herein are mostly non-aqueous compositions although they may comprise from 0% to 10% by weight of the total composition of water, preferably from 0% to 5%, more preferably from 0% to 1% and most preferably 0% by weight of the total composition of water.

In a preferred embodiment herein, the compositions herein are neutral compositions, and thus have a pH, as is measured at 25° C., of 6-8, more preferably 6.5-7.5, even more preferably 7.

In other preferred embodiment compositions have pH preferably above pH 4 and alternatively have pH preferably below pH 9.

In a preferred embodiment according to the present invention the compositions herein are thickened compositions. Preferably, the liquid compositions herein have a viscosity of up to 7500 cps at 20 s$^{-1}$, more preferably from 5000 cps to 50 cps, yet more preferably from 2000 cps to 50 cps and most preferably from 1500 cps to 300 cps at 20 s$^{-1}$ and 20° C. when measured with a Rheometer, model AR 1000 (Supplied by TA Instruments) with a 4 cm conic spindle in stainless steel, 2° angle (linear increment from 0.1 to 100 sec$^{-1}$ in max. 8 minutes).

In another preferred embodiment according to the present invention the compositions herein have a water-like viscosity. By "water-like viscosity" it is meant herein a viscosity that is close to that of water. Preferably the liquid compositions herein have a viscosity of up to 50 cps at 60 rpm, more preferably from 0 cps to 30 cps, yet more preferably from 0 cps to 20 cps and most preferably from 0 cps to 10 cps at 60 rpm and 20° C. when measured with a Brookfield digital viscometer model DV II, with spindle 2.

In a preferred embodiment the composition comprises one or more active ingredients preferably selected from the group consisting of surfactants especially comprising nonionic, anionic, zwitterionic, cationic, amphoteric and mixtures thereof, solvent especially comprising alcohol and/or ether-derived solvent, cleaning and/or surface active and/or suspending polymers, enzymes, malodor counteractants, perfumes, fluoride, xylitol, and mixtures thereof.

General examples of suitable active ingredients can be found in McCutcheon's "Emulsifiers and Detergents" (MC Publishing Co). or in "Handbook of Detergent" part A-F (M.Dekker/CRC/Surfactant science series) or "Surfactants and Polymers in aqueous solution" (Wiley) or "Enzymes in Detergency" (CRC). Suitable perfume compounds and compositions for use herein are for example those described in EP-A-0 957 156 under the paragraph entitled "Perfume", on page 13. The malodor counteractant, when present, is preferably selected from the group consisting of uncomplexed cyclodextrin; odor blockers; reactive aldehydes; flavanoids; zeolites; activated carbon; and mixtures thereof, as described in detail in WO03/089561 A2, on pages 9 to 15. The maolodor counteractant may be capsulated or un-capsulated. Compositions herein that comprise odor control agents can be used in methods to reduce or remove malodor from surfaces treated with the compositions.

Preferably, the composition herein comprises from 0.01% to 35% by weight of the total composition of a surfactant or a mixture thereof, more preferably from 0.5% to 20%, and most preferably from 1% to 10%.

The compositions herein may contain one or more further optional ingredients.

Abrasive Particles

The liquid cleaning and/or cleansing composition herein comprise abrasive cleaning particles that are selected or synthesized to feature very effective shapes, e.g. defined by macroshape and mesoshape descriptors whereas effective shape of particles are obtained by reducing a foam material into particles. Such particles are particles comprising inorganic materials, preferably wherein the inorganic is comprised at a level of greater than 60%, preferably greater than 80%, more preferably greater than 95%, even more preferably is 100%, by weight of the particle. It has been found that utilizing inorganics as materials for such particles introduces advantages as to weight efficiency and suspension ability, as well as providing good cleaning.

It is highly preferred that the particles be non-rolling. The applicant has found that non-rolling and/or sharp abrasive cleaning particles provide good soil removal and still provide low surface damage. The applicant has found that very specific particle shapes can be obtained from inorganic-based foam that provide the above cited benefits.

Additionally, the abrasive particles have preferably a multitude of sharp edges which are typical features of particles produced from foam structures defined by the present invention. The sharp edges of the non-spherical particles are defined by edges having a tip radius below 20 µm, preferably below 8 µm, most preferably from 5 µm to 0.5 µm. The tip radius is defined by the diameter of an imaginary circle fitting the curvature of the edge extremity. The applicant has found that particles obtained from grinding inorganic-based foams typically feature particles with sharp edges that are the result of the foaming process and specific open cell structure associated with foams. Blowing agents, either gas or volatilized solvent optionally with/without addition of tensioactifs or polymeric agents, help during the foaming process to sharpen the foam material edges (or struts) owing to the curvature of the expanding bubble.

FIG. 1 is an illustration of tip radius.

The abrasive particles are composed of the same foam material from which they are produced.

The production processes of the inorganic foam material are several and can be achieved with agglomerant additives to stabilize the foam structure at any given step of the inorganic foam manufacturing process.

Incidentally, the final inorganic foam product may contain residues of agglomerants to provide sufficient mechanical resistance. In that case, the level agglomerant is below 40%, preferably below 20%, most preferably below 5% weight by weight of the final inorganic-based foam. The agglomerant can be based on thermoplastic or crosslinkable polymer, wax, resin, glue, cellulosic, lingo-cellulosic material etc and mixtures. Typical examples of agglomerants are cellulosic polymers and fibers, dextrin, polyolefin especially polyethylene, polypropylene, polyvinyl acetate, polyvinyl alcohol, resin especially rosin ester, Polyolefin wax, montan wax and carnauba wax.

The agglomerant mixture may also contain fillers in the form of bead, particles or fibers. Fillers can be selected from the group consisting of polyethylene, polypropylene, PVC, polycarbonate, melamine, urea, polyurethane, polyacrylate, polystyrene, phenolic, polyesters, polyamide, natural material derived from cellulose, lingo-cellulose or shell such as nut shell, apple seeds, olive stones, apricot seed, kernel, wood, bamboo and plants and mixtures thereof. When filler are added with agglomerants, the total mass of filler and agglomerant is below 40%, preferably below 20%, most preferably below 5% weight by weight of the final inorganic-based foam.

In preferred embodiment, the final inorganic-based foam contains no agglomerant and no fillers as the results of a foaming process not requesting the presence of agglomerant at any given step of the manufacture process or that one or several curing or sintering steps of the inorganic-based foam are applied at elevated temperature to eliminate organic material and especially the agglomerant and filler. When a sintering step is present and no agglomerates are present in the generated inorganic foam, resulting in inorganic consisting particles, then the hardness of the agglomerate or its weight content vis-à-vis the inorganic material is no longer as important.

By via of this mean, the skilled person can formulate cleaning particle with selected material density and porosity to optimize the weight efficiency for cleaning.

Various suitable processes are well known and described in the art to achieve the foam structure with inorganic material therefore it is not the intention to describe in detail all processes and process detail. Nonetheless, preferred processes are mentioned below:

Process via Emulsion alternatively inverse emulsion e.g.: such as a process called polyHIPE (e.g.: polymerization of HIPE: High Internal Phase Emulsion or also described as Concentrated Water-in-Oil Emulsion) whereas the continuous phase contains the slurry inorganic precursor material (e.g.: with or without agglomerant and fillers) whereas the inorganic precursor material is further after solidified or cured. The solidification or curing step may occur before or after removal of the emulsified media.

Physical expansion foaming process: The foam structure is achieved by injecting or generating bubble gas within the slurry inorganic precursor material (with or without agglomerant and fillers) followed by controlled bubble expansion, stabilization (e.g.: with selected surfactant, polymers, particles or fiber) and solidification or curing steps. Expanding bubble can be made of injected gas under pressure (e.g.: air, CO2, N2) or made of blowing agent typically low boiling point blowing agent e.g.: pentane, cyclopentane, heptanes, water) or generated in-situ (e.g.: CO2). In a preferred embodiment the slurry inorganic precursor material contains also foaming polyurethane precursors e.g.: diisocyanate (e.g.: lupranate series from BASF) diols (e.g.: Lupranol serie from BASF), catalyst and emulsifier eg.: Niax series from Momentive). In this case, a minimum of 40% weight of polyurethane material is present to ensure effective foaming in presence of the inorganic slurry whereas after foaming is completed, a sintering step is necessary to eliminate the overload of the polyurethane.

Replicate or templating foaming process: In a highly preferred embodiment the inorganic comprising particles are produced from a inorganic-based foam generated via a process called replicate foaming. This process includes the steps of preparing a liquid slurry with the desired inorganic (in powder form) well dispersed therein, and impregnating a polymeric foam with such slurry, typically by immersion of the polymeric foam into the slurry in a vacuum to ensure the slurry penetrates throughout the entire reticular structure of the foam, followed by a curing step to solidify the inorganic such that the shape of the polymeric foam is replicated. Preferably such process comprises a sintering step wherein the polymeric foam is allowed to evaporate to leave the inorganic-based foam with entirely hollow struts forming the open cell network. Then after the grinding of the foam, shaped particle with hollow structure are created whereas the hollow structure improves the weight efficiency of the cleaning particle but constitutes equally a reservoir to transport and deliver actives to the surface such as surfactant, surface-active polymers, perfume, malodor counteractants, etc.

Freeze-casting process: Equally, the inorganic comprising particles are produced from a inorganic-based foam generated via a process called freeze-casting. This process includes the steps of dispersing the desired inorganic (in powder form) in a medium that is in liquid form at the temperature of dispersion, typically water, to generate a sol. The sol is then placed in a mold and frozen at a predetermined freezing rate, such that dendritic formation occurring during the freezing step generates an intricate array of branches agglomerating the inorganic at its interface. The freezing step is typically followed by a freeze-drying step to ensure the medium undergoes sublimation, i.e. a phase transition directly from solid to gas (typically by controlling temperature and pressure) such that the branches are effectively replaced by hollow channels giving the required porosity. The resulting porous structure is then cured such to solidify the inorganic in order to attain a inorganic-based foam with the required mechanical strength. It is herein understood that mediums other than water can be equally used, for example mediums wherein sublimation occurs at room temperature and pressure.

The applicant has found that efficacious and safe cleaning particles can be produced from foams with very specific structural parameters as described below.

Figure 2:
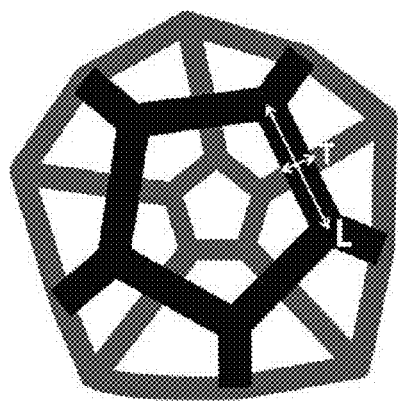
FIG. 2 is an illustration showing how to calculate foam strut aspect ratio.

Foam Strut Aspect Ratio:

Similarly, the applicant has found that a good cleaning effect can be achieved with abrasive particles which have been made from the foams featuring struts with high aspect ratios. By struts, the applicant defines the elongated material that interconnect to form the cellular structure of the foam, which is best described as a pentagonal dodecahedron structure for the foams as shown in FIG. 2. The strut length (L) is typically counted as the distance between the geometrical centers of 2 interconnecting knots. The struts thickness (T) is typically the projected strut thickness at the middle of the strut length. The applicant has understood that particles that are derived from foam presenting struts with excessively small L/T ratio present sub-optimal shapes for cleaning since likely to produce rounder particles that readily roll. On the contrary, the particles that are derived from foam presenting struts with excessively high L/T ratio also present sub-optimal shape for cleaning since they are likely to produce excessive amount of rod-like particles featuring low soil removal. Incidentally, the applicant has surprisingly found that significantly better cleaning effect can be achieved with struts having an L/T ratio ranging from 1.5 to 10, preferably from 2.0 to 8.0 and more preferably from 3.0 to 6.0 and most preferred from 3.5 to 4.5 as defined by Visiocell software.

FIG. 2 Pentagonal dodecahedron structure with struts length (L) and thickness (T)

In a preferred embodiment, in order to favor the reduction of the foam into particles, the foam is sufficiently brittle, i.e. upon stress, the foam has little tendency to deform but rather will break into particles.

Foam Density:

The applicant has found that a good cleaning effect can be achieved with abrasive particles which have been made from foam having a density above $100\gamma$ kg/m$^3$, and even up to $500\gamma$ kg/m$^3$, wherein $\gamma$ (as used herein) is the specific gravity of the inorganic. However the applicant has surprisingly found that a significantly better cleaning effect can be achieved with a foam density below $100\gamma$ kg/m$^3$, more preferably with a foam density from $50\gamma$ kg/m$^3$ to $100\gamma$ kg/m$^3$ and most preferably with a foam density from $5\gamma$ kg/m$^3$ to $50\gamma$ kg/m$^3$. Foam density can be measured, for instance, using the protocol described in ASTM D3574.

Foam Cell Size:

Similarly, the applicant has found that a good cleaning effect can be achieved with abrasive particles which have been made from foams featuring cell sizes ranging from 20 micrometers to 2000 micrometers. However the applicant has surprisingly found that a significantly better cleaning effect can be achieved with foams featuring cell sizes between 100-1000 micrometers, more preferably from 200 to 500 micrometers and most preferably from 300 to 450 micrometers. Foam cell size can be measured for instance using the protocol described in ASTM D3576.

Foam Open/Closed Cell Content:

Similarly, the applicant has found that a good cleaning effect can be achieved with abrasive particles which have been made from foams featuring close-cell structures. However, the applicant has surprisingly found that a significantly better cleaning effect can be achieved with abrasive cleaning particles, which have been reduces into particles from foams with open-cell structure. An open-cell foam structure presents the opportunity to form well defined sharp struts, which in turn produce effective abrasive particles. On the contrary, the presence of closed cells, wherein each cell is closed by foam material extending from each strut into a membrane-like material, produce after grinding into abrasive particles an abrasive population that contains a fraction of flat-shaped residue. This flat-shaped residue is not providing effective cleaning performance, and therefore, is undesirable feature. The shape of this flat-shaped residue is sub-optimal to deliver cleaning. Additionally, these membranes are inherently very fragile and are easily broken into significantly small particles, including undesirable dust, with sizes ranging from several hundred micrometers to sub-micrometer sizes during the grinding of the foam and also during use in the cleaning process. The applicant has found that foam structures with less than 50%, preferably less than 30%, and most preferably less than 15% of closed cells are desirable in producing effective abrasive cleaning particles.

Efficient cleaning particles are therefore produced by grinding the foam structure with special care to target size and shape. Hence for instance, when large particle size is desired, foam with large cell size is desirable and vice-et-versa. Additionally, in order to preserve an optimal particle shape while grinding the foam structure, it is recommended to not target particle size excessively below the dimension of the cell size of the foam. Typically, the applicant recommends targeting particle size not below about half of the foam cell size. The applicant has found that excessive particle reduction e.g.: vis-à-vis the original foam structure and especially vis-à-vis the cell size yields rounder particles with sub-optimal cleaning efficiency.

In practice, the process to reduce the foam into particle population is set such as the amount of particles with size below half of the average foam cell size is below 30% by weight, preferably below 20% more preferably below 10% and most preferably no particles are detected, whereas the particle size weight proportion is defined by physical sieving method. Note: In order to proceed to the separation of the particles based on size related to half of the average foam cell size, a tolerance of 10% is accepted for the selection of the sieving mesh vis-à-vis the theoretical target sieving grid. The selected sieving mesh tolerance is valid for smaller available sieving mesh vs. the theoretical target size.

One suitable way of reducing the foam to the abrasive cleaning particles herein is to grind or mill the foam. Other suitable means include the use of eroding tools such as a high speed eroding wheel with dust collector wherein the surface of the wheel is engraved with a pattern or is coated with abrasive sandpaper or the like to promote the foam to form the abrasive cleaning particles herein.

Alternatively and in a highly preferred embodiment herein, the foam may be reduced to particles in several stages. First the bulk foam can be broken into pieces of a few cm dimensions by manually chopping or cutting, or using a mechanical tool such as a lumpbreaker, for example the Model 2036 from S Howes, Inc. of Silver Creek, N.Y.

Hardness of the Abrasive Particles:

Preferred abrasive cleaning particles suitable for used herein are hard enough to provide good cleaning/cleansing performance, whilst providing a good surface safety profile.

Inorganic comprising particles for use in the present invention have a MOHS hardness of from 1 to 4, preferably from 1.5 to 3.5, preferably from 2 to 3, more preferably from 2.5 to below 3.

The MOHS hardness scale is an internationally recognized scale for measuring the hardness of a compound versus a compound of known hardness, see Encyclopedia of Chemical Technology, Kirk-Othmer, 4th Edition Vol 1, page 18 or Lide, D.R (ed) CRC Handbook of Chemistry and Physics, 73 rd edition, Boca Raton, Fla.: The Rubber Company, 1992-1993. Many MOHS Test kits are commercially available containing material with known MOHS hardness. For measurement and selection of abrasive material with selected MOHS hardness, the MOHS hardness measurement is typically carried out with un-shaped particles e.g.: with spherical or granular forms of the abrasive material.

In order to control that the foam-derived particles feature effective shape, it is useful in the present invention to define shape method and critical shape target parameters The shape of the abrasive cleaning particle can be defined in many ways. The present invention defines cleaning particle shape in a form of particle, which reflects the geometrical proportions of a particle and more pragmatically of a particles population. Very recent analytical techniques allow an accurate simultaneous measurement of particle shape from a large number of particles, typically greater than 10000 particles (preferably above 100 000). This enables accurate tuning and/or selection of average particle population shape with discriminative performance. These measurements analyse of particle shape are conducted using Occhio Nano 500 Particle Characterisation Instrument with its accompanying software Callistro version 25 (Occhio s.a. Liege, Belgium). This instrument is used to prepare, disperse, image and analyse the particle samples, as per manufacturer's instructions, and the following instrument setting selections: White Requested=180, vacuum time=5000 ms, sedimentation time=5000 ms, automatic threshold, number of particles counted/analyses=8000 to 500000, minimum number of replicates/sample=3, lens setting 1×/1.5×.

The applicant has considered although that the shape of particle of significant size play a critical role so in practice, the shape parameter are measured as mean shape of a particle population after exclusion of particles with size lower than 10 micrometers. Exclusion can be done either physically with help of sieve or preferably electronically via statistic filtering of particles with size diameter e.g.: "Area diameter" (the value of the diameter of a disc that has the same area A as the particle), below 10 micrometers (cf. ISO 9276-6:2008(E) section 7)

In the present invention shape descriptors are calculations of geometrical descriptors/shape factors. Geometrical shape factors are ratios between two different geometrical properties, such properties are usually a measure of proportions of the image of the whole particle or a measure of the proportions of an ideal geometrical body enveloping the particle or forms an envelope around the particle. These results are macroshape descriptors similar to aspect ratio, however the Applicant has discovered that mesoshape descriptors—a specific sub-class of macroshape descriptor—are particularly critical to the cleaning effectiveness and surface safety performances of the abrasive cleaning particles, while more typical shape parameters such as aspect ratio was proved insufficient. These mesoshape descriptors are a great help in defining how different a particle is compared to an ideal geometrical shape, especially how different compared to a sphere, and incidentally help define its ability for non-rolling, e.g.: sliding, effective cleaning movement pattern. The abrasive cleaning particles of the present invention are different from typical spherical or spherical-resembling e.g.: granular, abrasives forms.

Form Factor:

Form factor is a quantitative, 2-dimension image analysis shape description and is being measured according to ISO 9276-6:2008(E) section 8.2 as implemented via the Occhio Nano 500 Particle Characterisation Instrument with its accompanying software Callistro version 25 (Occhio s.a. Liege, Belgium). Form factor is a preferred mesoshape descriptor and is widely available in shape analysis instrument such as in Occhio Nano 500 or in Malvern Morphologi G3. Form factor is sometimes described in literature as being the difference between a particle's shape and a perfect sphere. Form factor values range from 0 to 1, where a form factor of 1 describes a perfectly spherical particles or disc particle as measured in a two dimensional image.

$$\text{Form Factor} = \frac{4\pi A}{P^2}$$

Where A is projection area, which is 2D descriptor and P is the length of the perimeter of the particle.

Inorganic comprising particles herein have a mean form factor of from 0.1 to 0.6 preferably from 0.1 to 0.4, preferably from 0.15 to 0.3 and more preferably from 0.2 to 0.25. Such are provide better cleaning performance and surface safety. Wherein mean data are extracted from volume-based vs. number-based measurements.

Figure 3:
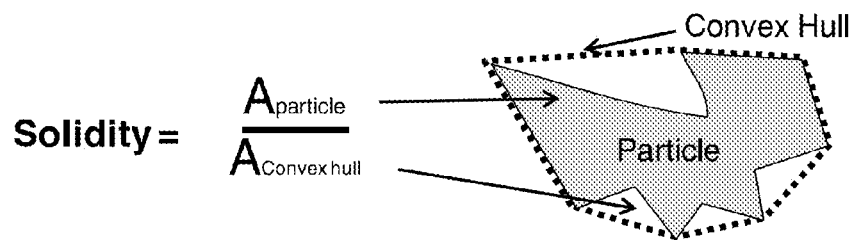
FIG. 3 is an illustration of the convex hull area and particle area.

Solidity:

Solidity is a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). The non-spherical particle herein has preferably at least one edge or surface having a concave curvature. Solidity is a mesoshape parameter, which describes the overall concavity of a particle/particle population. Solidity values range from 0 to 1, where a solidity number of 1 describes a non-concave particle, as measured in literature as being:

$$\text{Solidity} = A/Ac$$

Where A is the area of the particle and Ac is the area of the convex hull (envelope) of bounding the particle, see FIG. 3.

Inorganic comprising particles herein have a mean solidity from 0.3 to 0.9, preferably from 0.3 to 0.8, preferably from 0.5 to 0.7, and more preferably from 0.55 to 0.65. Wherein mean data are extracted from volume-based vs. number-based measurements. Such particles provide improved cleaning performance and surface safety Solidity is sometime also named Convexity in literature or in some apparatus software using the solidity formula in place of its definition described in ISO 9276-6 (convexity=Pc/P where P is the length of the perimeter of the particle and $P_C$ is length of the perimeter of the convex hull–envelope-bounding the particle). Despite solidity and convexity being similar mesoshape descriptor in concept, the applicant refers herein to the solidity measure expressed above by the Occhio Nano 500, as indicated above.

Optionally, the particles with above defined mesoshape descriptors may be mixed with more granular/spherical type of abrasives. In that case, the applicant considers the mesoshape value range applies to the final mix.

In highly preferred embodiment the abrasive cleaning particles have a mean solidity from 0.3 to 0.8 (preferably solidity from 0.5 to 0.7, and more preferably from 0.55 to 0.65), and/or a mean form factor from 0.1 to 0.4 (preferably from 0.15 to 0.3 and more preferably from 0.2 to 0.25).

By the term "mean form factor" or "mean solidity", the applicant consider the average of the form factor or solidity values of each particle taken from a population of at least 10 000 particles, preferably above 50 000 particles, more preferably above 100 000 particles, after excluding from the measurement and calculation, the form factor or solidity data of particles having area-equivalent diameter (ECD) of below 10 microns. Mean data are extracted from volume-based vs. number-based measurements.

Preferably, the non-spherical particles herein have a multitude of sharp edges. The sharp edges of the non-spherical particles are defined by edge having a tip radius below 20 μm, preferably below 8 μm, most preferably below 5 μm. The tip radius is defined by the diameter of an imaginary circle fitting the curvature of the edge extremity.

In a preferred embodiment, the abrasive cleaning particles have a mean ECD from 10 μm to 1000 μm, preferably from 50 μm to 500 μm, more preferably from 100 μm to 350 μm and most preferably from 150 to 250 μm, or from 10 μm to 50 μm, preferably 10 μm to 30 μm, more preferably 10 μm to 20 μm (particularly when such particles are used in toothpaste compositions).

Indeed, the Applicant has found that the abrasive particle size can be critical to achieve efficient cleaning performance whereas excessively abrasive population with small particle sizes e.g.: typically below 10 microns feature polishing action vs. cleaning despite featuring a high number of particles per particle load in cleaner inherent to the small particle size. On the other hand, abrasive population with excessively high particle size, e.g.: typically above 1000 micrometers, delivers not optimal cleaning efficiency since the number of particles per particle load in cleaner decreases significantly inherently to the large particle size. Additionally, excessively small particle size are not desirable in cleaner/for cleaning task since in practice, small and numerous particles are often hard to remove from the various surface topologies which requires excessive effort to remove from the user unless leaving the surface with visible particles residue. On the other hand, excessively large particle are too easily detected visually or provide bad tactile experience while handling or using the cleaner. Therefore, the applicant defines herein an optimal particle size range that deliver both optimal cleaning performance and usage experience.

The abrasive particles have size defined by their area-equivalent diameter (9276-6:2008(E) section 7) also called Equivalent Circle Diameter ECD (ASTM F1877-05 Section 11.3.2). Mean ECD of particle population is calculated as the average of respective ECD of each particles of a particle population of at least 10 000 particles, preferably above 50 000 particles, more preferably above 100 000 particles after excluding from the measurement and calculation the data of particles having area-equivalent diameter (ECD) of below 10 microns. Mean data are extracted from volume-based vs. number-based measurements.

In one preferred example, the size of the abrasive cleaning particles used in the present invention is modified during usage especially undergoing significant size reduction. Hence the particle remain visible or tactile detectable in liquid composition and at the start of the usage process to provide effective cleaning. As the cleaning process progresses, the abrasive particles disperse or break into smaller particles and become invisible to an eye or tactile undetectable.

It has surprisingly been found that the abrasive cleaning particles of the present invention show a good cleaning performance even at relatively low levels, such as preferably from 0.1% to 20% by weight of the total composition, preferably from 0.1% to 10%, more preferably from 0.5% to 5%, even more preferably from 1.0% to 3%, by weight of the total composition of said abrasive cleaning particles.

The particles used in the present invention can be white, transparent or colored by use of suitable dyes and/or pigments. Additionally suitable color stabilizing agents can be used to stabilize desired color. The abrasive particles are preferable color stable particles. By "color stable" it is meant herein that color of the particles used in the present invention will not turn yellow during storage and use.

In one preferred example, the abrasive cleaning particles used in the present invention remain visible when liquid composition is stored into a bottle while during the effective cleaning process abrasive particles disperse or break into smaller particles and become invisible to an eye.

Selection of Suitable Inorganics:

Inorganics to be used for the inorganic comprising particles are selected from those having a MOHS hardness of from 1 to 4, preferably from 1.5 to 3.5, preferably from 2 to 3, more preferably from 2.5 to 3, as measured using the test method described herein.

In a preferred embodiment, the inorganics used herein have a specific gravity ϒ of from 1 to 3, preferably from 1 to 2.5, more preferably from 1 to 2. The aforementioned specific gravity is selected such that the inorganic comprising particles deposit quickly onto a surface upon application of the liquid, providing effective cleaning, but at the same time are easy to suspend in a liquid matrix.

Typical inorganic material of interest are derived from carbonate, sulphate, phosphate hydroxide, fluoride salts of Calcium, Bairum, Iron, Magnesium, Manganese, Zinc, Copper, Borate, sodium, potassium, ammonium, alumina or silicate and blends whereas the material can be synthesized from extensively known inorganic synthesis processes (e.g.: Synthesis of Inorganic Materials—Wiley or Handbook of Inorganic Compounds—CRC) or extracted from mining & processing natural occurring inorganic material, alternatively be a mix of synthetic and natural material at any step of the manufacturing process of the inorganic foam. Example of inorganic precursors involve organic, oxide, hydroxide or halide of inorganic compounds optionally blended with natural inorganic material under the form of ultra-fine powder optionally with agglomerants. In that case, the fine powder is desirably below 30 micron, preferably below 15 microns, and more preferably below 5 microns to achieve best material homogeneity and synthesis success. In general, but especially when the starting inorganic precursor material contains fine powder of natural inorganic, a curing step, typically a sintering step is necessary to cure and cement the slurry and optionally to eliminated part or totality of the organic agglomerant. Generally the sintering temperature is above 400° C., preferably above 600° C.

Examples of natural inorganics for use herein may be selected from the group consisting of the inorganics listed in table 1 and the mixture thereof.

TABLE 1 suitable inorganics having MOHS hardness of from 1 to 4, wherein L is the lower limit and H is the higher limit.

| Name | MOHS (L) | MOHS (H) |
|---|---|---|
| Manganocalcite | 1 | 2 |
| Aliettite | 1 | 2 |
| Aluminite | 1 | |
| Coalingite | 1 | 2 |
| Coyoteite | 1 | 1.5 |
| Halloysite | 1 | 2.5 |
| Hectorite | 1 | 2 |
| Huntite | 1 | 2 |
| Illite | 1 | 2 |
| montmorillonite | 1 | 2 |
| Motukoreaite | 1 | 1.5 |
| Sauconite | 1 | 2 |
| Soapstone or steatite | 1 | 2.5 |
| Taranakite | 1 | 2 |
| Nontronite | 1.5 | 2 |
| Struvite | 1.5 | 2 |
| Baricite | 1.5 | 2 |
| Birnessite | 1.5 | |
| Covellite | 1.5 | 2 |
| Dickite | 1.5 | 2 |
| Gypsum | 1.5 | 2 |
| Pickeringite | 1.5 | 2 |
| Pyrophyllite | 1.5 | 2 |
| Saponite | 1.5 | |
| Sideronatrite | 1.5 | 2 |
| Stichtite | 1.5 | 2 |
| Todorokite | 1.5 | |
| Tschermigite | 1.5 | 2 |
| Vermiculite | 1.5 | 2 |
| Vivianite | 1.5 | 2 |
| Abelsonite | 2 | 3 |
| Admontite | 2 | 3 |
| Alabandite | 2 | |
| alabaster | 2 | |
| Ameghinite | 2 | 3 |
| attapulgite | 2 | 2.5 |
| Aubertite | 2 | 3 |
| Aurichalcite | 2 | |
| Bentorite | 2 | |
| Bilinite | 2 | |
| Botryogen | 2 | |
| Celadonite | 2 | |
| Cesanite | 2 | 3 |
| Chamosite | 2 | 2.5 |
| Clinochlore | 2 | 2.5 |
| Cyanotrichite | 2 | |
| Epsomite | 2 | 2.5 |
| Ettringite | 2 | 2.5 |
| Fibroferrite | 2 | 2.5 |
| Glauconite | 2 | |
| Glauconite | 2 | |
| Hydrotalcite | 2 | |
| Hydrozincite | 2 | 2.5 |
| Inyoite | 2 | |
| Kaolinite | 2 | 2.5 |
| Magadiite | 2 | |
| Manasseite | 2 | |
| Mohrite | 2 | 2.5 |
| Muscovite | 2 | 2.5 |
| Nimite | 2 | 2.5 |

TABLE 1-continued suitable inorganics having MOHS hardness of from 1 to 4, wherein L is the lower limit and H is the higher limit.

| Name | MOHS (L) | MOHS (H) |
|---|---|---|
| Palygorskite | 2 | 2.5 |
| Pennantite | 2 | 2.5 |
| Phlogopite | 2 | 2.5 |
| Pitticite | 2 | 3 |
| Proustite | 2 | 2.5 |
| Quintinite | 2 | |
| Saliotite | 2 | 3 |
| Selenite | 2 | |
| Sepiolite | 2 | |
| Serpentine | 2 | 4 |
| Shigaite | 2 | |
| Tuzlaite | 2 | 3 |
| Vashegyite | 2 | 3 |
| Aksaite | 2.5 | |
| Amarantite | 2.5 | |
| Amarillite | 2.5 | 3 |
| Anglesite | 2.5 | 3 |
| Artinite | 2.5 | |
| Bianchite | 2.5 | |
| Biotite | 2.5 | 3 |
| Blödite | 2.5 | 3 |
| Brammallite | 2.5 | 3 |
| Brushite | 2.5 | |
| Carnallite | 2.5 | |
| Chrysocolla | 2.5 | 3.5 |
| Chrysotile | 2.5 | 3 |
| Copiapite | 2.5 | 3 |
| Crocoite | 2.5 | 3 |
| Cryolite | 2.5 | 3 |
| Defernite | 2.5 | 3 |
| Digenite | 2.5 | 3 |
| Djurleite | 2.5 | 3 |
| Gibbsite | 2.5 | 3 |
| Gunningite | 2.5 | |
| Gyrolite | 2.5 | |
| Hemetite | 2.5 | |
| Hisingerite | 2.5 | 3 |
| Jarosite | 2.5 | 3.5 |
| Kernite | 2.5 | 3 |
| Kinoite | 2.5 | |
| Kurnakovite | 2.5 | 3 |
| Lansfordite | 2.5 | |
| Lepidolite | 2.5 | 3 |
| Löweite | 2.5 | 3 |
| Nesquehonite | 2.5 | |
| Paragonite | 2.5 | 3 |
| Phosphorrösslerite | 2.5 | |
| Portlandite | 2.5 | 3 |
| Pyrargyrite | 2.5 | |
| Pyroaurite | 2.5 | |
| Quenstedtite | 2.5 | |
| Schwertmannite | 2.5 | 3.5 |
| Sjögrenite | 2.5 | |
| Stevensite | 2.5 | |
| Tobermorite | 2.5 | |
| Ulexite | 2.5 | |
| Vanadinite | 2.5 | 3 |
| Whewellite | 2.5 | 3 |
| wulfenite | 2.5 | 3 |
| Aerinite | 3 | |
| Afwillite | 3 | 4 |
| Allophane | 3 | |
| Antlerite | 3 | 3.5 |
| Atacamite | 3 | 3.5 |
| Barite | 3 | 3.5 |
| Barrerite | 3 | 4 |
| Boleite | 3 | 3.5 |
| Bornite | 3 | 3.25 |
| Cacoxenite | 3 | 4 |
| Calcite | 3 | |
| Celestite | 3 | 3.5 |
| Cerussite | 3 | 3.5 |
| Connellite | 3 | |
| Dawsonite | 3 | |
| Diadochite | 3 | 4 |

TABLE 1-continued suitable inorganics having MOHS hardness of from 1 to 4,
wherein L is the lower limit and H is the higher limit.

| Name | MOHS (L) | MOHS (H) |
|---|---|---|
| Fluellite | 3 | |
| Hardystonite | 3 | 4 |
| Herbertsmithite | 3 | 3.5 |
| Heulandite | 3 | 4 |
| Heulandite | 3 | 3.5 |
| Hopeite | 3 | 3.5 |
| Laueite | 3.0 | |
| Leightonite | 3 | |
| Millerite | 3 | 3.5 |
| Mordenite | 3 | 4 |
| Newberyite | 3 | 3.5 |
| Priceite | 3 | 3.5 |
| Rhodesite | 3 | 4 |
| Verdite | 3 | |
| Whiteite | 3 | 4 |
| Witherite | 3 | 3.5 |
| Anapaite | 3.5 | |
| Ankerite | 3.5 | 4 |
| Magnesite | 3.5 | 4 |
| Ajoite | 3.5 | |
| Aragonite | 3.5 | 4 |
| Aragonte | 3.5 | 4 |
| Azurite | 3.5 | 4 |
| Brochantite | 3.5 | 4 |
| Calciborite | 3.5 | |
| Chalcopyrite | 3.5 | |
| Clinoptilolite | 3.5 | 4 |
| Cuprite | 3.5 | 4 |
| Dolomite | 3.5 | 4 |
| Erionite | 3.5 | 4 |
| Fluckite | 3.5 | 4 |
| Howlite | 3.5 | |
| Hydromagnesite | 3.5 | |
| Jennite | 3.5 | |
| Kutnohorite | 3.5 | 4 |
| Macdonaldite | 3.5 | 4 |
| Magnesite | 3.5 | 4 |
| Malachite | 3.5 | 4 |
| Northupite | 3.5 | 4 |
| Polyhalite | 3.5 | |
| Powellite | 3.5 | 4 |
| Rhodochrosite | 3.5 | 4 |
| Robertsite | 3.5 | |
| Shattuckite | 3.5 | |
| Siderite | 3.5 | 4 |
| Sphalerite | 3.5 | 4 |
| Stilbite | 3.5 | 4 |
| Tarbuttite | 3.5 | |
| Thaumasite | 3.5 | |
| Vauxite | 3.5 | |
| Wavellite | 3.5 | 4 |
| weloganite | 3.5 | |
| Siderite | 3.75 | 4 |
| Barytocalcite | 4 | |
| Alunite | 4 | |
| Augelite | 4 | |
| Bobfergusonite | 4 | |
| Creedite | 4 | |
| Cyrilovite | 4 | |
| Fluorite | 4 | |
| Gatehouseite | 4 | |
| Laumontite | 4 | |
| Margarite | 4 | |
| Partheite | 4 | |
| Rosasite | 4 | |
| Sampleite | 4 | |
| Weddellite | 4 | |

In a preferred embodiment the inorganics to be used for the inorganic comprising particles are selected from those having a MOHS hardness of from 2 to 3 and a specific gravity of from 1 to 2.5. Preferably, such inorganics are selected from the group consisting of those listed in table 2 and mixtures thereof.

TABLE 2 suitable inorganics having MOHS hardness ranging from 2 to 3
and specific gravity of from 1 to 2.5, wherein L is the lower limit
and H is the higher limit.

| Name | MOHS (L) | MOHS (H) | Specific Gravity |
|---|---|---|---|
| Palygorskite | 2 | 2.5 | 1 |
| Abelsonite | 2 | 3 | 1.33 |
| Epsomite | 2 | 2.5 | 1.67 |
| Phosphorrösslerite | 2.5 | | 1.72 |
| Pickeringite | 1.5 | 2 | 1.73 |
| Mohrite | 2 | 2.5 | 1.8 |
| Nesquehonite | 2.5 | | 1.82 |
| Fibroferrite | 2 | 2.5 | 1.84 |
| Kurnakovite | 2.5 | 3 | 1.847 |
| Bilinite | 2 | | 1.87 |
| Chrysocolla | 2.5 | 3.5 | 1.93 |
| Vashegyite | 2 | 3 | 1.93 |
| Montmorillonite | 1 | 2 | 2 |
| Halloysite | 1 | 2 | 2 |
| Artinite | 2.5 | | 2 |
| Hydrotalcite | 2 | | 2 |
| Diadochite | 3 | 4 | 2 |
| Manasseite | 2 | | 2 |
| Bianchite | 2.5 | | 2.03 |
| Copiapite | 2.5 | 3 | 2.08 |
| Sjögrenite | 2.5 | | 2.08 |
| Heulandite | 3 | 3.5 | 2.1 |
| Mordenite | 3 | 4 | 2.1 |
| Pyroaurite | 2.5 | | 2.1 |
| Newberyite | 3 | 3.5 | 2.1 |
| Quenstedtite | 2.5 | | 2.11 |
| Fluellite | 3 | | 2.14 |
| Stevensite | 2.5 | | 2.15 |
| Amarantite | 2.5 | | 2.18 |
| Amarillite | 2.5 | 3 | 2.19 |
| Kaolinite | 2 | 2.5 | 2.2 |
| Cacoxenite | 3 | 4 | 2.2 |
| Whewellite | 2.5 | 3 | 2.2 |
| Pitticite | 2 | 3 | 2.2 |
| Portlandite | 2.5 | 3 | 2.2 |
| Sideronatrite | 1.5 | 2 | 2.2 |
| Heulandite-Na | 3 | 3.5 | 2.2 |
| Tuzlaite | 2 | 3 | 2.21 |
| Rhodesite | 3 | 4 | 2.27 |
| Gypsum | 2 | | 2.3 |
| Coalingite | 1 | 2 | 2.3 |
| Barrerite | 3 | 4 | 2.3 |
| Brushite | 2.5 | | 2.3 |
| Defernite | 3 | | 2.34 |
| Baricite | 1.5 | 2 | 2.35 |
| Löweite | 2.5 | 3 | 2.37 |
| Gibbsite | 2.5 | 3 | 2.38 |
| Glauconite | 2 | | 2.4 |
| Priceite | 3 | 3.5 | 2.4 |
| Hisingerite | 2.5 | 3 | 2.43 |
| Laueite | 3.0 | | 2.44 |
| Gyrolite | 2.5 | | 2.45 |

In a most preferred embodiment, the inorganics for use herein have a MOHS hardness of from 2.5 to 3 and a specific gravity of from 1 to 2. Preferably, the inorganic(s) is selected from the group consisting of those listed in table 3 and combinations thereof.

TABLE 3 suitable inorganics having MOHS hardness of from 2.5 to 3 and specific gravity of from 1 to 2, wherein L is the lower limit and H is the higher limit.

| Name | Formula | MOHS (L) | MOHS (H) | Specific Gravity |
|---|---|---|---|---|
| Palygorskite | $(Mg,Al)5(Si,Al)8O20(OH)2 \cdot 8H2O$ | 2 | 2.5 | 1 |
| Abelsonite | $Ni(C31H32N4)$ | 2 | 3 | 1.33 |
| Epsomite | $MgSO4 \cdot 7H2O$ | 2 | 2.5 | 1.67 |
| Phosphorrösslerite | $Mg(HPO4) \cdot 7H2O$ | 2.5 | | 1.72 |
| Mohrite | $(NH4)2Fe(SO4)2 \cdot 6H2O$ | 2 | 2.5 | 1.8 |
| Nesquehonite | $MgCO3 \cdot 3H2O$ | 2.5 | | 1.82 |
| Fibroferrite | $Fe3+(SO4)(OH) \cdot 5H2O$ | 2 | 2.5 | 1.84 |
| Kurnakovite | $Mg(H4B3O7)(OH) \cdot 5H2O$ | 2.5 | 3 | 1.847 |
| Chrysocolla | $Cu2-xAlx(H2-xSi2O5)(OH)4 \cdot nH2O$ (x < 1) | 2.5 | 3.5 | 1.93 |
| Vashegyite | $Al11(PO4)9(OH)6 \cdot 38H2O$ | 2 | 3 | 1.93 |
| Artinite | $Mg2(CO3)(OH)2 \cdot 3H2O$ | 2.5 | | 2 |
| Bianchite | $(Zn,Fe)SO4 \cdot 6H2O$ | 2.5 | | 2.03 |
| Copiapite | $Fe2+Fe3+4(SO4)6(OH)2 \cdot 20H2O$ | 2.5 | 3 | 2.08 |
| Sjögrenite | $Mg6Fe3+2(CO3)(OH)16 \cdot 4H2O$ | 2.5 | | 2.08 |

Inorganic comprising particles having the aforementioned characteristics, and in particular the cited specific gravity, allow for improved weight efficiency versus for example other similarly derived particles from polymeric materials and the like. Without wishing to be bound by theory, this is believed to be due to their higher density vs. polymer-derived cleaning particles, when higher density inorganic particles tend to sediment faster at the cleaning interface where the cleaning phenomenon occurs. As the cleaning formulation undergoes dilution with water, e.g.: present in the cleaning implement, the suspending system loses its suspension efficiency and more inorganic particles deposit faster at the cleaning interface vs. organic particles.

A further advantage of the inorganic comprising particles herein, is that in view of the higher weight efficiency, the total level of particles contained in the composition may be reduced vs. inorganic particles with excessive density e.g.: typically above 3.

The following inorganic materials are some examples of materials not useful in the present invention in view of their MOHs hardness being either below 1 or above 4: Anorthominasragrite, Anthoinite, Barberiite, Beryllite, Bostwickite, Carlinite, Dashkovaite, Dinite, Ekaterinite, Evenkite, Formicaite, Glaucocerinite, Griffithite, Hartite, Hornesite, Ilmajokite, Jungite, Larisaite, Lasalite, Lazarenkoite, Mangazeite, Matulaite, Meta-autunite, Nacrite, Natron, Cornetite, Direnzoite, Dusmatovite, Ekanite, Manganberzeliite, Natrophilite, Phosphoinnelite, Rosenhahnite, Bafertisite, Bederite, Bellbergite, Derbylite, Dilithium, Dioptase, Dittmarite, Lovozerite, Lukrahnite, Magbasite and the like.

Figure 4:
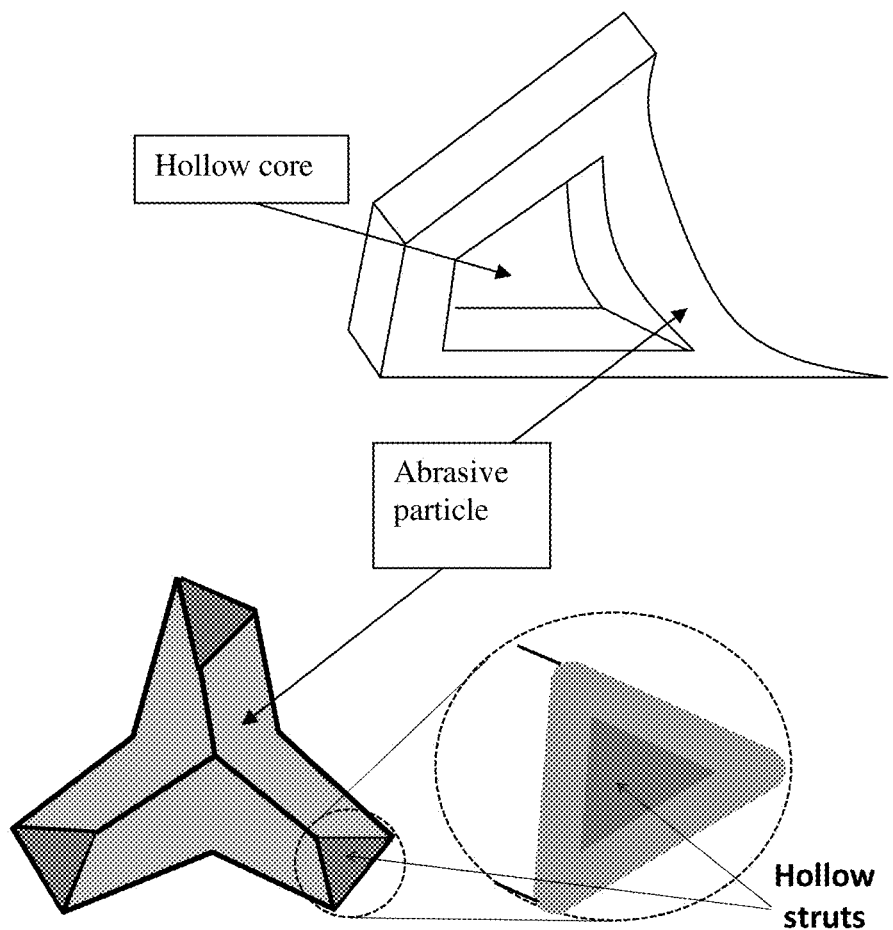
FIG. 4 is an illustration of an exemplary inorganic comprising particle having a hollow core.

In a preferred embodiment the inorganic comprising particles comprise a hollow core, as exemplified in FIG. 4. Such is typically achieved when the foam is produced via replicate foaming comprising a sintering step as described earlier. In this embodiment the core is typically filled with one or more active materials. One of the advantages of this embodiment is that the active ingredient is suddenly released upon application of shear during the wiping and/or rubbing process once the particles break up into smaller fragments, such enhancing the effective action of the active ingredients onto the surface treated. In this embodiment the active material is preferably selected from the group of surfactant, surface-active polymer malodor counteractant, perfume, and mixtures thereof. The use of such inorganic comprising particles having a malodor counteractant and/or perfume contained within their hollow core, in a liquid detergent composition, provides effective malodor removal from a hard surface.

In a preferred embodiment the hollow core is in fluid communication with the outside of the particle, preferably having an open end on at least one surface, more preferably more than one surface, such that the active material contained therein is not fully encapsulated but preferably retained via surface tension. The active material may be incorporated into the hollow particle by immersion in the active material while holding it under a vacuum.

Optional Ingredients

The compositions according to the present invention may comprise a variety of optional ingredients depending on the technical benefit aimed for and the surface treated.

Suitable optional ingredients for use herein include chelating agents, radical scavengers, surface-modifying polymers, solvents, builders, buffers, bactericides, hydrotropes, colorants, stabilizers, bleaches, bleach activators, suds controlling agents like fatty acids, enzymes, hydrophobic emollients, humectants, soil suspenders, brighteners, anti dusting agents, dispersants, pigments, and dyes.

Suspending Aid:

The abrasive cleaning particles present in the composition herein are typically solid particles in a liquid or paste composition. Said abrasive cleaning particles may be suspended in the liquid composition. However, it is well within the scope of the present invention that such abrasive cleaning particles are not-stably suspended within the composition and either settle or float on top of the composition. In this case, a user may have to temporally suspend the abrasive cleaning particles by agitating (e.g., shaking or stirring) the composition prior to use.

However, it is preferred herein that the abrasive cleaning particles are stably suspended in the liquid compositions herein. Thus the compositions herein comprise a suspending aid.

The suspending aid herein may either be a compound specifically chosen to provide a suspension of the abrasive cleaning particles in the liquid compositions of the present invention, such as a structurant, or a compound that also provides another function, such as a thickener or a surfactant (as described herein elsewhere).

Any suitable organic and inorganic suspending aids typically used as gelling, thickening or suspending agents in cleaning/cleansing compositions and other detergent or cosmetic compositions may be used herein. Indeed, suitable organic suspending aids include polysaccharide polymers. In addition or as an alternative, polycarboxylate polymer thickeners may be used herein. Also, in addition or as an alternative of the above, layered silicate platelets e.g.: Hectorite, bentonite or montmorillonites can also be used. Suitable commercially available layered silicates are Laponite RD® or Optigel CL® available from Rockwood Additives.

Suitable polycarboxylate polymer thickeners include (preferably lightly) crosslinked polyacrylate. A particularly suitable polycarboxylate polymer thickeners is Carbopol commercially available from Lubrizol under the trade name Carbopol 674®.

Suitable polysaccharide polymers for use herein include substituted cellulose materials like carboxymethylcellulose, ethyl cellulose, hydroxyethyl cellulose, hydroxypropyl cellulose, hydroxymethyl cellulose, succinoglycan and naturally occurring polysaccharide polymers like Xanthan gum, gellan gum, guar gum, locust bean gum, tragacanth gum, succinoglucan gum, or derivatives thereof, or mixtures thereof. Xanthan gum is commercially available from Kelco under the tradename Kelzan T.

Preferably the suspending aid herein is Xanthan gum. In an alternative embodiment, the suspending aid herein is a polycarboxylate polymer thickeners preferably a (preferably lightly) crosslinked polyacrylate. In a highly preferred embodiment herein, the liquid compositions comprise a combination of a polysaccharide polymer or a mixture thereof, preferably Xanthan gum, with a polycarboxylate polymer or a mixture thereof, preferably a crosslinked polyacrylate.

As a preferred example, Xanthan gum is preferably present at levels between 0.1% to 5% by weight of the total composition, more preferably from 0.5% to 2%, even more preferably from 0.8% to 1.2%.

Organic Solvent:

As an optional but highly preferred ingredient the composition herein comprises an organic solvents or mixtures thereof.

The compositions herein comprise from 0% to 30% by weight of the total composition of an organic solvent or a mixture thereof, more preferably 1.0% to 20% and most preferably, 2% to 15%.

Suitable solvents can be selected from the group consisting of: aliphatic alcohols, ethers and diethers having from 4 to 14 carbon atoms, preferably from 6 to 12 carbon atoms, and more preferably from 8 to 10 carbon atoms; glycols or alkoxylated glycols; glycol ethers; alkoxylated aromatic alcohols; aromatic alcohols; terpenes; and mixtures thereof. Aliphatic alcohols and glycol ether solvents are most preferred.

Aliphatic alcohols, of the formula R—OH wherein R is a linear or branched, saturated or unsaturated alkyl group of from 1 to 20 carbon atoms, preferably from 2 to 15 and more preferably from 5 to 12, are suitable solvents. Suitable aliphatic alcohols are methanol, ethanol, propanol, isopropanol or mixtures thereof. Among aliphatic alcohols, ethanol and isopropanol are most preferred because of their high vapour pressure and tendency to leave no residue.

Suitable glycols to be used herein are according to the formula HO—CR$_1$R$_2$—OH wherein R1 and R2 are independently H or a C$_2$-C$_{10}$ saturated or unsaturated aliphatic hydrocarbon chain and/or cyclic. Suitable glycols to be used herein are dodecaneglycol and/or propanediol.

In one preferred embodiment, at least one glycol ether solvent is incorporated in the compositions of the present invention. Particularly preferred glycol ethers have a terminal C$_3$-C$_6$ hydrocarbon attached to from one to three ethylene glycol or propylene glycol moieties to provide the appropriate degree of hydrophobicity and, preferably, surface activity. Examples of commercially available solvents based on ethylene glycol chemistry include mono-ethylene glycol n-hexyl ether (Hexyl Cellosolve®) available from Dow Chemical. Examples of commercially available solvents based on propylene glycol chemistry include the di-, and tri-propylene glycol derivatives of propyl and butyl alcohol, which are available from Arco under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, and mixtures thereof. "Butyl" includes normal butyl, isobutyl and tertiary butyl groups. Mono-propylene glycol and mono-propylene glycol mono-butyl ether are the most preferred cleaning solvent and are available under the tradenames Dowanol DPnP® and Dowanol DPnB®. Di-propylene glycol mono-t-butyl ether is commercially available from Arco Chemical under the tradename Arcosolv PTB®.

In a particularly preferred embodiment, the cleaning solvent is purified so as to minimize impurities. Such impurities include aldehydes, dimers, trimers, oligomers and other byproducts. These have been found to deleteriously affect product odour, perfume solubility and end result. The inventors have also found that common commercial solvents, which contain low levels of aldehydes, can cause irreversible and irreparable yellowing of certain surfaces. By purifying the cleaning solvents so as to minimize or eliminate such impurities, surface damage is attenuated or eliminated.

Though not preferred, terpenes can be used in the present invention. Suitable terpenes to be used herein monocyclic terpenes, dicyclic terpenes and/or acyclic terpenes. Suitable terpenes are: D-limonene; pinene; pine oil; terpinene; terpene derivatives as menthol, terpineol, geraniol, thymol; and the citronella or citronellol types of ingredients.

Suitable alkoxylated aromatic alcohols to be used herein are according to the formula R-(A)$_n$—OH wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols to be used herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Chelating Agents:

One class of optional compounds for use herein includes chelating agents or mixtures thereof. Chelating agents can be incorporated in the compositions herein in amounts ranging from 0.0% to 10.0% by weight of the total composition, preferably 0.01% to 5.0%.

Suitable phosphonate chelating agents for use herein may include alkali metal ethane 1-hydroxy diphosphonates (HEDP), alkylene poly (alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename ssEDDS® from Palmer Research Laboratories.

Suitable amino carboxylates for use herein include ethylene diamine tetra acetates, diethylene triamine pentaacetates, diethylene triamine pentaacetate (DTPA),N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FSS and methyl glycine di-acetic acid (MGDA).

Further carboxylate chelating agents for use herein include salicylic acid, aspartic acid, glutamic acid, glycine, malonic acid or mixtures thereof.

Radical Scavenger:

The compositions of the present invention may further comprise a radical scavenger or a mixture thereof.

Suitable radical scavengers for use herein include the well-known substituted mono and dihydroxy benzenes and their analogs, alkyl and aryl carboxylates and mixtures thereof. Preferred such radical scavengers for use herein include di-tert-butyl hydroxy toluene (BHT), hydroquinone, di-tert-butyl hydroquinone, mono-tert-butyl hydroquinone, tert-butyl-hydroxy anysole, benzoic acid, toluic acid, catechol, t-butyl catechol, benzylamine, 1,1,3-tris(2-methyl-4-hydroxy-5-t-butylphenyl) butane, n-propyl-gallate or mixtures thereof and highly preferred is di-tert-butyl hydroxy toluene. Such radical scavengers like N-propyl-gallate may be commercially available from Nipa Laboratories under the trade name Nipanox S1®.

Radical scavengers, when used, may be typically present herein in amounts up to 10% by weight of the total composition and preferably from 0.001% to 0.5%. The presence of radical scavengers may contribute to the chemical stability of the compositions of the present invention.

Dye:

The liquid compositions according to the present invention may be coloured. Accordingly, they may comprise a dye or a mixture thereof.

Delivery Form of the Compositions

The compositions herein may be packaged in a variety of suitable packaging known to those skilled in the art, such as plastic bottles for pouring liquid compositions, squeeze bottles or bottles equipped with a trigger sprayer for spraying liquid compositions. Alternatively, the paste-like compositions according to the present invention may by packaged in a tube.

In an alternative embodiment herein, the liquid composition herein is impregnated onto a substrate, preferably the substrate is in the form of a flexible, thin sheet or a block of material, such as a sponge.

Suitable substrates are woven or non-woven sheets, cellulosic material based sheets, sponge or foam with open cell structures e.g.: polyurethane foams, cellulosic foam, melamine foam, etc.

Process of Cleaning a Surface

In a preferred embodiment a surface, preferably a hard surface, is contacted with the composition according to the present invention, preferably wherein said composition is applied onto said surface.

In another preferred embodiment, the process herein comprises the steps of dispensing (e.g., by spraying, pouring, squeezing) the liquid composition according to the present invention from a container containing said liquid composition and thereafter cleaning and/or cleansing said surface.

The composition herein may be in its neat form or in its diluted form. By "in its neat form", it is to be understood that said liquid composition is applied directly onto the surface to be treated without undergoing any dilution, i.e., the liquid composition herein is applied onto the surface as described herein. By "diluted form", it is meant herein that said liquid composition is diluted by the user typically with water. The liquid composition is diluted prior to use to a typical dilution level of up to 10 times its weight of water. A usually recommended dilution level is a 10% dilution of the composition in water.

The composition herein may be applied using an appropriate implement, such as a mop, paper towel, brush (e.g., a toothbrush) or a cloth, soaked in the diluted or neat composition herein. Furthermore, once applied onto said surface said composition may be agitated over said surface using an appropriate implement. Indeed, said surface may be wiped using a mop, paper towel, brush or a cloth.

The process herein may additionally contain a rinsing step, preferably after the application of said composition. By "rinsing", it is meant herein contacting the surface cleaned/cleansed with the process according to the present invention with substantial quantities of appropriate solvent, typically water, directly after the step of applying the liquid composition herein onto said surface.

By "substantial quantities", it is meant herein between 0.01 lt. and 1 lt. of water per $m^2$ of surface, more preferably between 0.1 lt. and 1 lt. of water per $m^2$ of surface.

In a preferred embodiment herein, process of cleaning is a process of cleaning household hard surfaces with a liquid composition according to present invention.

EXAMPLES

These following compositions are made comprising the listed ingredients in the listed proportions (weight %). Examples 1-43 herein exemplify the present invention, but are not necessarily used to limit or otherwise define the scope of the present invention.

Example of Inorganic Foam 1

40 parts weight of Calcium carbonate or talk or gypsum and mixture are mixed with 40 parts weight of Voranol 3010

(Dow) or Lupranol 2040 (BASF), 2 part of Niax L620 (Momentive) and 1 part of polyurethance catalyst system (mix of tin octoate, dibutyltin dilaureate system, 1,4-diazabicyclooctane, triethylenediamine, dimethylethanolamine and water) and optionally 8 part of pentane. Note: the water content of the mix is then adjusted accordingly to the water content already in the Calcium carbonate, talk or gypsum selection. 40 part weight of Lupranate M200R (BASF) is added and through fully mixed for 1 minute. The skill person will adjust the level of catalyst, pentane and water as well as the reaction temperature to promote the foaming according to the desired final foam density. In the example herein foam density varying from 120-300 kg·m3 are easily achieved. The foam is then undergoing a sintering step at 700° C. for minimum 60 minutes whereas all organic residue from the polyurethane foam has been released leaving a skeleton of inorganic foam with density ranging 40-100 kg/m3, Mohs ranging 2-3. Calcium carbonate examples are Covercarb 60 (0.8 μm marble from Omya), Craie moulue (2.8 μm chalk, from Omya), Syncarb F0474-60 (1.8 μm calcite from Omya), Superfine S (2.2 μm chalk, from Omya), Sturcal FA4046 (2 μm from Specialty Minerals), Fintalc M30-SQ (9 μm talc from Mondo Mineral) and gypsum from Aldrich. Foam is ground to yield particle with Equivalent circle diameter of 250 μm.

Example of Inorganic Foam 2 a block of 20×100×100 cm or Open-cell, reticulated flexible foam of density 30 kg/km3 undergo a cycle of immersing/squeezing in a slurry calcium carbonate of covercarb 60 (CaCO3 from Omya, 72% solid content) or syncarb F0476-Go (CaCO3 from Omya, 52% solid content), w.wo Fintalc M30-SQ (powder talc from Mondo) until the density of the coated foam increases to minimum 2.5-5×. The foam is then dried at 200° C. for 60 minutes and submitted to a sintering step at 700° C. for minimum 60 minutes whereas all organic residue from the polyurethane foam has been released leaving a skeleton of inorganic foam with density ranging ~25-85 kg/m3 and Mohs 2.5-3. Foam is ground to yield particle with Equivalent circle diameter of 300 μm.

Example of Inorganic Foam 3 a block of 20×100×100 cm or Open-cell, reticulated flexible foam of density 30 kg/km3 undergo a cycle of immersing/squeezing in a slurry calcium carbonate of covercarb 60 (CaCO3 from Omya, 72% solid content) or syncarb F0476-Go (CaCO3 from Omya, 52% solid content), w.wo Fintalc M30-SQ (powder talc from Mondo) added with 5% dry weight equivalent of agglomerant (95% dry calcium carbonate-talk mix/5% agglomerant) until the density of the coated foam increases to minimum 2.5-5×. The foam is then dried at 200° C. for 60 minutes. Optionally the foam is submitted to a sintering step at 700° C. for minimum 60 minutes whereas all organic residue from the agglomerant has been released leaving a skeleton of inorganic foam with density ranging ~25-85 kg/m3 and Mohs 2.5-3. Example of agglomerants are Keltrol RD (xantan gum from CP kelco), NFC (microfibrillated cellulose from JRS), Arbocel UFC C3 (ultrafine cellulose 3 μm from JRS), Dextrolin 6743 (dextrin liquid adhesive from Paramelt), Luwax PE 10M micronized Polyethylene wax from BASF), Polygen MW1 (montan wax from BASF), Luwax S (acid montan wax from BASF), Polygen WE20 (High density oxidized polypropylene from BASF), Carnauba wax powder from Paramelt, Syncera CW 1245 (carnaubax wax emulsion from Paramelt), Kartofix (polyvinyl alcohol powder from Paramlelt), Enzyflex 318 (Polyvinyl acetate liquid adhesive from Paramelt) and mix. Foam is ground to yield particle with Equivalent circle diameter of 200 μm.

Example of Inorganic Foam 4 a block of 20×100×100 cm or Open-cell, reticulated flexible foam of density 30 kg/km3 undergo a cycle of immersing/squeezing in a slurry calcium hydroxide (CaOH2) and/or serpentine (Mg3SiO3(OH4) and/or dolomite (CaMg(CO$_3$) 2+SiO2 until the density of the coated foam increases to min. 2.5-5×. The foam is dried at 200° C. under CO2 atmosphere until the reaction of the CO2 with calcium hydroxide and/or serpentine and/or dolomite to form respectively calcium carbonate (with calcium carbonate) and/or talc (with Serpentine or dolomite). When desirably more efficient or faster results are required, the treatment with $CO_2$ may occur under high pressure and temperature condition e.g.: 200° C., 100 bars). The foam is then submitted to a sintering step at 700° C. for minimum 60 minutes yielding an inorganic foam with density ranging ~25-85 kg/m3 and Mohs 2.5-3. Foam is ground to yield particle with Equivalent circle diameter of 250 μm.

Example of Inorganic Foam 5

$CO_2$ is pressure-injected in a slurry calcium hydroxide (CaOH2) and/or serpentine (Mg3SiO3(OH4) and/or dolomite (CaMg(CO3)2+SiO$_2$) in presence of silicon-alkyl surfactant (e.g.: Niax L620 from Momentive) in order to reach 20× expansion ratio. The gas flow of CO2 is maintained until the CO2 reaction with calcium hydroxide and/or serpentine and/or dolomite is completed yielding an inorganic foam with density ranging ~25-50 kg/m3 and Mohs 2.5-3. Foam is ground to yield particle with Equivalent circle diameter of 100 μm.

Example of Inorganic Foam 6

40 parts weight of Calcium carbonate (Omyacarb 1TAV stearic coated, 1.7 μm from Omya or Superfine S stearic coated 2.2 μm chalk from Omya) or talk (Sturcal FA4046 stearic coated 2 μm from Specialty Minerals) or mix are mixed with 60 parts styrene/divinyl benzene mix (95/5), 2.5 part Span 80 and 1 part sodium persulfate. 3000 part of water with 120 part of CaCl2 are slowly added at 60° C. to create a high inverse phase emulsion. When achieved the emulsion is polymerized at 90° C. for 12 hr. The foam is then submitted to a sintering step at 700° C. for minimum 60 minutes yielding an inorganic foam with density ranging ~10-25 kg/m3 and Mohs 2.5-3. Foam is ground to yield particle with Equivalent circle diameter of 15 μm.

As example, the grinding of the inorganic foams into small particles is done using a rotary mill and the particle selection was done with used of air jet sieving instrument from Retsch.
Hard Surface Cleaner Bathroom Composition:

| | % Weight | | |
|---|---|---|---|
| | 1 | 2 | 3 |
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |

-continued

| | % Weight | | |
|---|---|---|---|
| | 1 | 2 | 3 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| Abrasive particles made from inorganic foam # 1 | 1 | 1 | 1 |
| Water | Balance | Balance | Balance |

Hard Surface Cleaner Bathroom Composition (Cont.):

| | % Weight | | |
|---|---|---|---|
| | 4 | 5 | 6 |
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| Abrasive particles made from inorganic foam # 1 | 2 | 2 | 2 |
| Water | Balance | Balance | Balance |

Hand-Dishwashing Detergent Compositions:

| | % Weight | | |
|---|---|---|---|
| | 7 | 8 | 9 |
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| Abrasive particles made from inorganic foam # 1 | 2 | 2 | 2 |
| Water (+minor e.g.; pH adjusted to 10.5) | Balance | Balance | Balance |

General Degreaser Composition:

| | % Weight | |
|---|---|---|
| | 10 | 11 |
| C9-C11 EO8 (Neodol 91-8 ®) | 3 | 3 |
| N-Butoxy Propoxy Propanol | 15 | 15 |
| Ethanol | 10 | 5 |
| Isopropanol | | 10 |
| Polysaccharide (Xanthan Gum-glyoxal modified Optixan-T) | 0.35 | 0.35 |
| Abrasive particles made from inorganic foam # 2 | 1 | 1 |
| Water (+minor e.g.; pH adjusted to alkaline pH) | Balance | Balance |

Scouring Composition:

| | % Weight | | |
|---|---|---|---|
| | 12 | 13 | 14 |
| Sodium C13-16 prafin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5 Mw | 0.75 | 0.75 | 0.75 |
| Diatomaceous earth (Celite 499 ® median size 10 μm) | 25 | | |
| Calcium Carbonate (Merk 2066 ® median size 10 μm) | | 25 | |
| Abrasive particles made from inorganic foam # 3 | 5 | 5 | 5 |
| Water | Balance | Balance | Balance |

Liquid Glass Cleaner:

| | % Weight | |
|---|---|---|
| | 15 | 16 |
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| Abrasive particles made from inorganic foam # 6 | 0.5 | 0.5 |
| Water (+minor) | Balance | Balance |

Cleaning Wipe (Body Cleansing Wipe):

| | % Weight | | |
|---|---|---|---|
| | 17 | 18 | 19 |
| C10 Amine Oxide | — | 0.02 | — |
| C12,14 Amine Oxide | 0.4 | — | — |
| Betaine (Rewoteric AM CAS 15 U) | — | — | 0.2 |
| C9,11 A5EO (Neodol E 91.5 ®) | — | 0.1 | — |
| C9,11 A8EO (Neodol E 91.8 ®) | — | — | 0.8 |
| C12,14 A5EO | 0.125 | — | — |
| 2-Ethyl Hexyl Sulphate | — | 0.05 | 0.6 |
| Silicone | 0.001 | 0.003 | 0.003 |
| EtOH | 9.4 | 8.0 | 9.5 |
| Propylene Glycol Butyl Ether | 0.55 | 1.2 | — |
| Geraniol | — | — | 0.1 |
| Citric acid | 1.5 | — | — |
| Lactic acid | — | — | 1.5 |
| Perfume | 0.25 | 0.15 | 0.15 |

-continued

| | % Weight | | |
|---|---|---|---|
| | 17 | 18 | 19 |
| Abrasive particles made from inorganic foam # 3 | 0.5 gram/sqm | 1 gram/sqm | 3 gram/sqm |
| Nonwoven: Spunlace 100% viscose 50 gsm (lotion loading fact) | | | (×3.5) |
| Nonwoven: Airlaid walkisoft (70% cellulose, 12% Viscose, 18% binder) 80 gsm (lotion loading factor) | | (×3.5) | |
| Carded thermobonded (70% polypropylene, 30% rayon), 70 gsm (Lotion loading factor) | (×3.5) | | |

Cleaning Wipe (Body Cleansing Wipe):

| | % Weight |
|---|---|
| | 20 |
| Benzalkonioum Chloride (Alkaquat DMB-451 ®) | 0.1 |
| Cocamine Oxide (C10/C16 alkyl dimethyl amine oxide; AO-1214 LP supplied by Procter & Gamble Co.) | 0.5 |
| Pyroglutamic Acid (pidolidone) (2-pyrrolidone-5 carboxylic acid) | 4 |
| Ethanol-denatured 200 proof (SD alcohol 40 ®) | 10 |
| DC Antiform H-10 (dimethicone) | 0.03 |
| Sodium Benzoate | 0.2 |
| Tetrasodium EDTA (Hampene 220 ®) | 0.1 |
| Sodium Chloride | 0.4 |
| Perfume | 0.01 |
| Water and minors | balance |

The above wipes lotion composition is loaded onto a water-insoluble substrate, being a patterned hydroentangled nonwoven substrate having a basis weight of 56 grams per square meter comprising 70% polyester and 30% rayon approximately 6.5 inches wide by 7.5 inches long with a caliper of about 0.80 mm. Optionally, the substrate can be pre-coated with dimethicone (Dow Corning 200 Fluid 5cst) using conventional substrate coating techniques. Lotion to wipe weight ratio of about 2:1 using conventional substrate coating techniques. Abrasive particles made from inorganic foam 4 are loaded on the wipe e.g.: via the wipe lotion in way to achieve 0.2-3 gram particles/sqm substrate Oral Care Composition (Toothpaste):

| | % Weight | |
|---|---|---|
| | 20 | 21 |
| Sorbitol (70% sol.) | 24.2 | 24.2 |
| Glycerin | 7 | 7 |
| Carboxymethylcellulose | 0.5 | 0.5 |
| PEG-6 | 4 | 4 |
| Sodium Fluoride | 0.24 | 0.24 |

-continued

| | % Weight | |
|---|---|---|
| | 20 | 21 |
| Sodium Saccharine | 0.13 | 0.13 |
| Mono Sodium phosphate | 0.41 | 0.41 |
| Tri Sodium phosphate | 0.39 | 0.39 |
| Sodium Tartrate | 1 | 1 |
| $TiO_2$ | 0.5 | 0.5 |
| Silica | 35 | |
| Sodium lauroyl sarcosinate (95% active) | 1 | 1 |
| Flavor | 0.8 | 0.8 |
| Abrasive particles made from inorganic foam # 6 | 2 | 5 |
| Water | Balance | Balance |

Body Cleansing Composition:

| | % Weight | |
|---|---|---|
| | 22 | 23 |
| Cocoamidopropyl betaine | 5.15 | 5.15 |
| Sodium Laureth sulfate | 5.8 | 5.8 |
| Sodium Lauroyl sarcosinate | 0.5 | 0.5 |
| Polyquaternium 10 | 0.1 | 0.1 |
| C12-14 fatty alcohol | 0.45 | 0.45 |
| Zinc Stearate | 1.5 | 1.5 |
| Glycol DiStearate | 0.25 | 0.25 |
| Sodium lauryl sulfate | 0.53 | 0.53 |
| Cocamidopropyl betaine | 0.17 | 0.17 |
| Lauramide Diethanolamide | 0.48 | 0.48 |
| Sodium sulfate | 0.05 | 0.05 |
| Citric Acid | 0.05 | 0.05 |
| DMDM hydantoin (1,3-Dimethylol-5,5-dimethylhydantoin Glydant) | 0.2 | 0.2 |
| Tetra Sodium EDTA | 0.1 | 0.1 |
| Fragance | 0.5 | 0.5 |
| Polysaccharide (Xanthan Gum-glyoxal modified Optixan-T) | 0.2 | 0.2 |
| Abrasive particles made from inorganic foam # 6 | 2 | 1 |
| Water and minors | | 1 |
| Water | Balance | Balance |

Facial Cleansing Compositions

| Ingredients | 24 | 25 | 26 | 27 |
|---|---|---|---|---|
| Acrylates Copolymer[1] | 1.50 | 2.0 | 1.25 | — |
| Acrylates/$C_{10-30}$ alkyl acrylate crosspolymer[2] | — | — | — | 1.0 |
| Sodium Lauryl Sulfate | 2.0 | — | — | — |
| Sodium Laureth Sulfate | 8.0 | — | — | — |
| Ammonium Lauryl Sulfate | — | 6.0 | — | — |
| Sodium Trideceth Sulfate | — | — | 3.0 | 2.5 |
| Sodium Myristoyl Sarcosinate | — | 2.0 | 3.0 | 2.5 |
| Sodium Lauroamphoacetate[3] | — | — | 6.0 | 5.0 |
| Sodium Hydroxide* | pH >6 | — | — | — |

-continued

| Ingredients | 24 | 25 | 26 | 27 |
|---|---|---|---|---|
| Triethanolamine* | — | pH >6 | — | pH 5.2 |
| Cocamidopropyl Betaine | 4.0 | 7.0 | — | — |
| Glycerin | 4.0 | 5.0 | 2.0 | 2.0 |
| Sorbitol | — | — | 2.0 | 2.0 |
| Salicylic Acid | — | — | 2.0 | 2.0 |
| Fragrance | 0.1 | 0.1 | 0.1 | 0.1 |
| Preservative | 0.3 | 0.3 | 0.15 | 0.15 |
| Abrasive particles made from inorganic foam # 5 | 1.0 | 1.0 | 2.0 | 2.0 |
| PEG 120 Methyl Glucose Trioleate[4] | 0.5 | — | 0.25 | 0.25 |
| PEG 150 Pentaerythrityl Tetrastearate[5] | — | 0.40 | — | — |
| Citric Acid** | pH 5.5 | pH 5.5 | pH 5.5 | pH 5.5 |
| Water | QS to 100% | QS to 100% | QS to 100% | QS to 100% |

*per the supplier use directions, the base is used to activate the acrylates copolymer
**acid can be added to adjust the formula to a lower pH
[1]Carbopol Aqua SF-1 ® from Noveon ™, Inc.
[2]Carbopol Ultrez 21 ® from Noveon ™, Inc.
[3]Miranol ® Ultra L32 from Rhodia
[4]Glucamate LT ® from Chemron
[5]Crothix ® from Croda Examples 24 to 27 are Made the Following Way:

Add Carbopol® to de-ionized free water of the formulation. Add all surfactants except cationics and betaines. If the pH is less than 6 then add a neutralizing agent (typically a base i.e., Triethanolamine, sodium hydroxide) to adjust to a pH greater than 6. If necessary, apply gentle heat to reduce viscosity and help minimize air entrapment. Add betaine and/or cationic surfactants. Add conditioning agents, additional rheology modifiers, pearlizing agents, encapsulated materials, exfoliants, preservatives, dyes, fragrances, abrasive particles and other desirable ingredients. Lastly, if desired reduce the pH with an acid (i.e. citric acid) and increase viscosity by adding sodium chloride.

Oral Care Composition (Toothpaste)

| | 28 | 29 | 30 | 31 | 32 |
|---|---|---|---|---|---|
| Sodium Gluconate | 1.064 | 1.064 | 1.064 | 1.064 | 0.600 |
| Stannous fluoride | 0.454 | 0.454 | 0.454 | 0.454 | 0.454 |
| Sodium fluoride | | | | | |
| Sodium monofluorophosphate | | | | | |
| Zinc Lactate | 0.670 | 0.670 | 0.670 | 0.670 | 2.500 |
| Glycerin | — | — | — | — | 36.000 |
| Polyethylene glycol 300 | | | | | 7.000 |
| Propylene Glycol | | | | | 7.000 |
| Sorbitol(LRS) USP | 39.612 | 39.612 | 39.612 | 39.612 | — |
| Sodium lauryl sulfate solution (28%) | 5.000 | 5.000 | 5.000 | 5.000 | 3.500 |
| Abrasive particles made from inorganic foam # 1 | 10.000 | 10.000 | 1.000 | 5.000 | 5.000 |
| Zeodent 119 | — | — | — | — | — |
| Zeodent 109 | | | 10.000 | 10.000 | 10.000 |
| Hydrogen peroxide (35% soln) | | | | | |
| Sodium hexametaphosphate | — | — | — | — | 13.000 |
| Gantrez | | 2.000 | 2.000 | 2.000 | — |
| Natural CaCO3-600M | — | — | — | — | — |
| Sodium phosphate (mono basic) | — | — | — | — | — |
| Sodium phosphate (Tri basic) | — | — | — | — | 1.000 |
| Zeodent 165 | — | — | — | — | — |
| Cocoamidopropyl Betaine (30% Soln) | — | — | — | — | — |
| Cetyl Alcohol | 3.000 | — | — | — | — |
| Stearyl Alcohol | 3.000 | — | — | — | — |
| Hydroxyethyl cellulose (HEC Natrasol 250M) | — | 0.500 | 0.500 | 0.500 | — |
| CMC 7M8SF | — | 1.300 | 1.300 | 1.300 | — |
| Xanthan Gum | — | — | — | — | 0.250 |
| Poloxamer 407 | — | — | — | — | — |
| Carrageenan mixture | — | 0.700 | 0.700 | 0.700 | 0.600 |
| Titanium dioxide | — | — | — | — | — |
| Saccharin Sodium | 0.500 | 0.500 | 0.500 | 0.500 | 0.500 |

-continued

|  | 28 | 29 | 30 | 31 | 32 |
|---|---|---|---|---|---|
| Flavor | 1.000 | 1.000 | 1.000 | 1.000 | 1.000 |
| Water | QS | QS | QS | QS | QS |

Zeodent 119, 109 and 165 are precipitated silica materials sold by the J. M. Huber Corporation.
Gantrez is a copolymer of maleic anhydride or acid and methyl vinyl ether.
CMC 7M8SF is a sodium carboxymethylcellulose.
Poloxamer is a difunctional block-polymer terminating in primary hydroxyl groups.

|  | 33 | 34 | 35 | 36 | 37 |
|---|---|---|---|---|---|
| Sodium Gluconate | — | — | — | — | — |
| Stannous fluoride | — | — | — | — | — |
| Sodium fluoride | — | 0.243 | 0.243 | 0.243 | — |
| Sodium monofluorophosphate | 1.10 | — | — | — | — |
| Zinc Lactate | — | — | — | — | — |
| Glycerin | — | — | — | — | 40.000 |
| Polyethylene glycol 300 | — | — | — | — | — |
| Propylene Glycol | — | — | — | — | — |
| Sorbitol(LRS) USP | 24.000 | 42.500 | 42.500 | 42.500 | 30.000 |
| Sodium lauryl sulfate solution (28%) | 4.000 | 4.000 | — | 4.000 | — |
| Abrasive particles made from inorganic foam # 1 | 5.000 | 10.000 | 10.000 | 5.000 | 15.000 |
| Zeodent 119 | — | — | — | 10.000 | — |
| Zeodent 109 | | | | | |
| Hydrogen peroxide (35% soln) | | | | | |
| Sodium hexametaphosphate | — | — | — | — | — |
| Gantrez | | | | | |
| Natural CaCO3-600M | 35.00 | — | — | — | — |
| Sodium phosphate (mono basic) | 0.10 | 0.420 | 0.420 | 0.420 | 0.420 |
| Sodium phosphate (Tri basic) | 0.40 | 1.100 | 1.100 | 1.100 | 1.100 |
| Zeodent 165 | 2.00 | — | — | — | 2.000 |
| Cocoamidopropyl Betaine (30% Soln) | — | — | 5.000 | — | — |
| Cetyl Alcohol | 0.000 | — | — | — | — |
| Stearyl Alcohol | 0.000 | — | — | — | — |
| Hydroxyethyl cellulose (HEC Natrasol 250M) | — | 0.500 | 0.500 | 0.500 | — |
| CMC 7M8SF | 1.300 | 1.300 | 1.300 | 1.300 | 1.300 |
| Xanthan Gum | — | — | — | — | — |
| Poloxamer 407 | — | — | — | — | — |
| Carrageenan mixture | — | 0.700 | 0.700 | 0.700 | — |
| Titanium dioxide | — | — | — | — | — |
| Saccharin Sodium | 0.250 | 0.500 | 0.500 | 0.500 | 0.500 |
| Flavor | 1.000 | 1.000 | 1.000 | 1.000 | 1.000 |
| Water | QS | QS | QS | QS | QS |

|  | 38 | 39 | 40 |
|---|---|---|---|
| Sodium Gluconate | — | — | 1.500 |
| Stannous fluoride | — | — | 0.454 |
| Sodium fluoride | — | — | — |
| Sodium monofluorophosphate | — | — | — |
| Zinc Lactate | — | — | — |
| Glycerin | 40.000 | 10.000 | 25.000 |
| Polyethylene glycol 300 | 3.000 | — | — |
| Propylene Glycol | — | — | — |
| Sorbitol(LRS) USP | — | 39.612 | — |
| Sodium lauryl sulfate solution (28%) | 5.000 | 4.000 | 4.000 |
| Abrasive particles made from inorganic foam # 1 | 15.000 | 5.000 | 5.000 |
| Zeodent 119 | — | — | — |
| Zeodent 109 | | | |
| Hydrogen peroxide (35% soln) | — | 8.570 | 8.570 |
| Sodium hexametaphosphate | 14.000 | — | — |
| Gantrez | | | |
| Natural CaCO3-600M | — | — | — |
| Sodium phosphate (mono basic) | 0.420 | — | — |
| Sodium phosphate (Tri basic) | 1.100 | — | — |
| Zeodent 165 | 2.000 | — | — |
| Cocoamidopropyl Betaine (30% Soln) | — | — | — |
| Cetyl Alcohol | — | 3.000 | — |
| Stearyl Alcohol | — | 3.000 | — |
| Hydroxyethyl cellulose (HEC Natrasol 250M) | — | — | — |
| CMC 7M8SF | 1.000 | — | — |
| Xanthan Gum | 0.300 | — | — |
| Poloxamer 407 | 0.500 | — | 18.000 |
| Carrageenan mixture | — | — | — |
| Titanium dioxide | 0.500 | — | — |
| Saccharin Sodium | 0.500 | 0.500 | 0.500 |
| Flavor | 1.000 | 1.000 | 1.000 |
| Water | QS | QS | QS |

Hair Shampoo

|  | 41 | 42 | 43 |
|---|---|---|---|
| Water | q.s. | q.s. | q.s. |
| Polyquaterium 76[1] | 0.25 | — | — |
| Guar, Hydroxylpropyl Trimonium Chloride[2] | — | 0.25 | — |
| Polyquaterium 6[3] | — | — | 0.25 |
| Sodium Laureth Sulfate | 12 | 10.5 | 10.5 |
| Sodium Lauryl Sulfate | | 1.5 | 1.5 |
| Silicone[4] | 0.75 | 1.00 | 0.5 |
| Cocoamidopropyl Betaine | 3.33 | 3.33 | 3.33 |
| Cocoamide MEA | 1.0 | 1.0 | 1.0 |
| Ethylene Glycol Distearate | 1.50 | 1.50 | 1.50 |
| Abrasive particles made from inorganic foam # 1 | 1 | | 2 |
| Crosslinked PS-DVB (50% DVB 55, mean diameter D(v, 0.9) 75 μm) abrasive cleaning particles | | 1 | |
| Fragrance | 0.70 | 0.70 | 0.70 |
| Preservatives, pH & Visc. adjusters | Up to 1% | Up to 1% | Up to 1% |

[1]Copolymer of Acrylamide(AM) and TRIQUAT, MW = 1,000,000; CD = 1.6 meq./gram; Rhodia
[2]Jaguar C500, MW-500,000, CD = 0.7, Rhodia
[3]Mirapol 100S, 31.5% active, Rhodia
[4]Dimethicone Fluid, Viscasil 330M; 30 micron particle size; Momentive Silicones The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising abrasive particles derived from inorganic-based foam, wherein said abrasive particles are non-spherical having a form factor from about 0.1 to about 0.6 and a solidity from about 0.3 to about 0.9, and wherein said abrasive particles comprise one or more inorganic materials and have a MOHs hardness of from about 1 to about 4, wherein the one or more inorganic materials are selected from the group consting of: manganocalcite, aliettite, aluminite, coalingite, coyoteite, halloysite, hectorite, huntite, illite, montmorillonite, motukoreaite, sauconite, soapstone or steatite, taranakite, nontronite, struvite, barićite, birnessite ,covellite, dickite, gypsum, pickeringite, pyrophyllite, saponite, sideronatrite, stichtite, todorokite, tschermigite, vermiculite, vivianite, abelsonite, admontite, alabandite, alabaster, ameghinite, attapulgite, aubertite, aurichalcite, bentorite, bilinite, botryogen, celadonite, cesanite, chamosite, clinochlore, cyanotrichite, epsomite, ettringite, fibroferrite, glauconite, glauconite, hydrotalcite, hydrozincite, inyoite, kaolinite, magadiite, manasseite, mohrite, muscovite, nimite, palygorskite, pennantite, phlogopite, pitticite, proustite, quintinite, saliotite, selenite, sepiolite, serpentine, shigaite, tuzlaite, vashegyite, aksaite, amarantite, amarillite, anglesite, artinite, bianchite, biotite, blödite, brammallite, brushite, carnallite, chrysocolla, chrysotile, copiapite, crocoite, cryolite, defernite, digenite, djurleite, gibbsite, gunningite, gyrolite, hemetite, hisingerite, jarosite, kernite, kinoite, kurnakovite, lansfordite, lepidolite, löweite, nesquehonite, paragonite, phosphorösslerite, portlandite, pyrargyrite, pyroaurite, quenstedtite, schwertmannite, sjögrenite, stevensite, tobermorite, ulexite, vanadinite, whewellite, wulfenite, aerinite, afwillite, allophane, antlerite, atacamite, barite, barrerite, boleite, bornite, cacoxenite, calcite, celestite, cerussite, connellite, dawsonite, diadochite, fluellite, hardystonite, herbertsmithite, heulandite, heulandite, hopeite, laueite, leightonite, millerite, mordenite, newberyite, priceite, rhodesite, verdite, whiteite, witherite, anapaite, ankerite, magnesite, ajoite, aragonite, aragonte, azurite, brochantite, calciborite, chalcopyrite, clinoptilolite, cuprite, dolomite, erionite, fluckite, howlite, hydromagnesite, jennite, kutnohorite, macdonaldite, magnesite, malachite, northupite, polyhalite, powellite, rhodochrosite, robertsite, shattuckite, siderite, sphalerite, stilbite, tarbuttite, thaumasite, vauxite, wavellite, weloganite, siderite, barytocalcite, alunite, augelite, bobfergusonite, creedite, cyrilovite, fluorite, gatehouseite, laumontite, margarite, partheite, rosasite, sampleite, weddellite, and combinations thereof.

2. A composition according to claim 1 wherein the composition is a liquid or paste, and wherein said composition further comprises one or more ingredients selected from the group consisting of solvents, surface-active polymers, malodor counteractants, perfumes, enzymes, fluoride, xylitol, and mixtures thereof.

3. A composition according to claim 1 wherein the inorganic material is comprised at a level of greater than about 60% by weight of the abrasive particle.

4. A composition according to claim 1 wherein the inorganic-based foam has an open cell structure.

5. A composition according to claim 1 wherein the abrasive particles have a form factor from about 0.1 to about 0.4 and a solidity of from about 0.3 to about 0.8.

6. A composition according to claim 1 wherein said abrasive particles have a MOHs hardness of from about 1.5 to about 3.5.

7. A composition according to claim 1 wherein the abrasive particles have a specific gravity of from about 1 to about 3.

8. A composition according to claim 1 wherein the particles comprise one or more agglomerates, said agglomerants being selected from the group consisting of cellulosic polymers, fibers, and combinations thereof.

9. A composition according to claim 1 wherein the abrasive particles comprise a hollow core.

10. A composition according to claim 1 wherein the inorganic-based foam is formed by a process selected from the group consisting of replicate foaming, physical expansion foaming, emulsion expansion foaming, and freeze-casting.

11. A composition according to claim 9 wherein the core comprises at least one active ingredient.

12. A composition according to claim 11 wherein the active ingredient consists of one or more materials selected from the group consisting of surfactants, solvents, perfumes, malodor counteractants and mixtures thereof, and wherein the core is impregnated or filled with said active ingredient.

13. A process comprising the steps of:
(i) fragmenting a inorganic-based foam to generate abrasive particles comprising one or more inorganic materials, wherein the one or more inorganic materials are selected from the group consting of: manganocalcite, aliettite, aluminite, coalingite, coyoteite, halloysite, hectorite, huntite, illite, montmorillonite, motukoreaite, sauconite, soapstone or steatite, taranakite, nontronite, struvite, barićite, birnessite ,covellite, dickite, gypsum, pickeringite, pyrophyllite, saponite, sideronatrite, stichtite, todorokite, tschermigite, vermiculite, vivianite, abelsonite, admontite, alabandite, alabaster, ameghinite, attapulgite, aubertite, aurichalcite, bentorite, bilinite, botryogen, celadonite, cesanite, chamosite, clinochlore, cyanotrichite, epsomite, ettringite, fibroferrite, glauconite, glauconite, hydrotalcite, hydrozincite, inyoite, kaolinite, magadiite, manasseite, mohrite, muscovite, nimite, palygorskite, pennantite, phlogopite, pitticite, proustite, quintinite, saliotite, selenite, sepiolite, serpentine, shigaite, tuzlaite, vashegyite, aksaite, amarantite, amarillite, anglesite, artinite, bianchite, biotite, blödite, brammallite, brushite, carnallite, chrysocolla, chrysotile, copiapite, crocoite, cryolite, defernite, digenite, djurleite, gibbsite, gunningite, gyrolite, hemetite, hisingerite, jarosite, kernite, kinoite, kurnakovite, lansfordite, lepidolite, löweite, nesquehonite, paragonite, phosphorrosslerite, portlandite, pyrargyrite, pyroaurite, quenstedtite, schwertmannite, sjögrenite, stevensite, tobermorite, ulexite, vanadinite, whewellite, wulfenite, aerinite, afwillite, allophane, antlerite, atacamite, barite, barrerite, boleite, bornite, cacoxenite, calcite, celestite, cerussite, connellite, dawsonite, diadochite, fluellite, hardystonite, herbertsmithite, heulandite, heulandite, hopeite, laueite, leightonite, millerite, mordenite, newberyite, priceite, rhodesite, verdite, whiteite, witherite, anapaite, ankerite, magnesite, ajoite, aragonite, aragonte, azurite, brochantite, calciborite, chalcopyrite, clinoptilolite, cuprite, dolomite, erionite, fluckite, howlite, hydromagnesite, jennite, kutnohorite, macdonaldite, magnesite, malachite, northupite, polyhalite, powellite, rhodochrosite, robertsite, shattuckite, siderite, sphalerite, stilbite, tarbuttite, thaumasite, vauxite, wavellite, weloganite, siderite, barytocalcite, alunite, augelite, bobfergusonite, creedite, cyrilovite, fluorite, gatehouseite, laumontite, margarite, partheite, rosasite, sampleite, weddellite, and combinations thereof;

(ii) providing one or more surfactants; and (iii) forming a liquid composition by combining the abrasive particles with the one or more surfactants, wherein said abrasive particles are non-spherical having a form factor from about 0.1 to about 0.6 and a solidity from about 0.3 to about 0.9, and wherein said abrasive particles have a MOHs hardness of from about 1 to about 4.

\* \* \* \* \*